United States Patent [19]

Kopecek et al.

[11] Patent Number: 5,258,453
[45] Date of Patent: Nov. 2, 1993

[54] DRUG DELIVERY SYSTEM FOR THE SIMULTANEOUS DELIVERY OF DRUGS ACTIVATABLE BY ENZYMES AND LIGHT

[75] Inventors: Jindrich Kopecek; Nancy L. Krinick, both of Salt Lake City, Utah

[73] Assignee: University of Utah, Salt Lake City, Utah

[21] Appl. No.: 822,924

[22] Filed: Jan. 21, 1992

[51] Int. Cl.$^5$ .................. C08G 63/48; C08G 63/91; A61L 9/01
[52] U.S. Cl. .................. 525/54.1; 424/78.17; 424/78.18; 424/78.31; 530/811; 530/812; 530/815; 530/816
[58] Field of Search .................. 525/54.1; 526/238.1, 526/238.2; 530/811, 812, 815, 816; 424/78.17, 78.18, 78.31; 514/17, 18, 19, 25, 27, 29, 31, 32, 33, 34, 35, 37, 39, 80, 82, 183, 185, 422, 443, 561, 616, 625, 636

[56] References Cited

U.S. PATENT DOCUMENTS 5,037,883  8/1991  Kopecek et al. .................. 526/238.1

OTHER PUBLICATIONS

Krinick "Synthesis of N-(2-Hydroxypropyl)Methacrylamide Copolymer-Anti-Thy 1,2 Antibody-Chlorin $e_6$ Conjugates and a Preliminary Study of Their Photodynamic Effect on Mouse Splenocytes in vitro" Makrol. Chem., 191, 839-856 (1990).

Dougherty "Photoradiation Therapy for Cutaneous and Subcutaneous Malignancies" J. of Invest., Dermatology 77: 122-124, 1981.

Kopecek et al "Targetable Photoactivatable Polymeric Drugs" J. of Cont. Release 16 (1991) 137-144.

Primary Examiner—Nathan M. Nutter
Attorney, Agent, or Firm—Thorpe, North & Western

[57] ABSTRACT

Compositions for the treatment of cancerous tissues in warm-blooded animals containing both an anticancer drug and a photoactivatable drug attached to copolymeric carriers are made up of a member selected from the group consisting of (a) a copolymeric carrier having attached thereto both an anticancer drug and a photoactivatable drug, (b) a mixture of copolymeric carriers wherein one copolymeric carrier has attached an anticancer drug and the other copolymeric carrier has attached a photoactivatable drug and (c) a combination of (a) and (b). The anticancer drug is attached to the polymeric carrier by side-chains which are stable in the blood stream of the warm-blooded animal but susceptible to hydrolysis by lysosomal enzymes intracellularly. The photoactivatable drug is attached by either the same degradable side-chain or by a non-degradable attachment. The polymer carrier may optionally contain a targeting moiety. Upon administration polymeric macromolecules enter targeted cancer cells by pinocytosis which reduces the side effects normally elicited by the free drugs. A time lag is allowed following administration for optimal uptake of the copolymers in the cancerous tissue for the anticancer agent to begin to take effect. Then a light sources of the appropriate wavelength and energy is to activate the photoactivatable drug. The combined effect of the anticancer agent and photoactivatable drug provides greater cell destruction at reduced dosages and side effects.

31 Claims, No Drawings

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 4
        ( B ) TYPE: amino acid
        ( D ) TOPOLOGY: linear ( x i ) SEQUENCE DESCRIPTION: SEQ ID NO:1:

Gly Phe Leu Gly ( 2 ) INFORMATION FOR SEQ ID NO:2:

( i ) SEQUENCE CHARACTERISTICS:
        ( A ) LENGTH: 4
        ( B ) TYPE: amino acid
        ( D ) TOPOLOGY: linear ( x i ) SEQUENCE DESCRIPTION: SEQ ID NO:2:

Gly Phe Phe Leu ( 2 ) INFORMATION FOR SEQ ID NO:3:

( i ) SEQUENCE CHARACTERISTICS:
        ( A ) LENGTH: 4
        ( B ) TYPE: amino acid
        ( D ) TOPOLOGY: linear ( x i ) SEQUENCE DESCRIPTION: SEQ ID NO:3:

Gly Leu Leu Gly ( 2 ) INFORMATION FOR SEQ ID NO:4:

( i ) SEQUENCE CHARACTERISTICS:
        ( A ) LENGTH: 4
        ( B ) TYPE: amino acid
        ( D ) TOPOLOGY: linear ( x i ) SEQUENCE DESCRIPTION: SEQ ID NO:4:

Gly Phe Tyr Ala ( 2 ) INFORMATION FOR SEQ ID NO:5:

( i ) SEQUENCE CHARACTERISTICS:
        ( A ) LENGTH: 4
        ( B ) TYPE: amino acid
        ( D ) TOPOLOGY: linear ( x i ) SEQUENCE DESCRIPTION: SEQ ID NO:5:

Gly Phe Gly Phe ( 2 ) INFORMATION FOR SEQ ID NO:6:

(i) SEQUENCE CHARACTERISTICS:
 (A) LENGTH: 4
 (B) TYPE: amino acid
 (D) TOPOLOGY: linear (xi) SEQUENCE DESCRIPTION: SEQ ID NO:6:

Ala Gly Val Phe (2) INFORMATION FOR SEQ ID NO:7:

(i) SEQUENCE CHARACTERISTICS:
 (A) LENGTH: 4
 (B) TYPE: amino acid
 (D) TOPOLOGY: linear (xi) SEQUENCE DESCRIPTION: SEQ ID NO:7:

Gly Phe Phe Gly (2) INFORMATION FOR SEQ ID NO:8:

(i) SEQUENCE CHARACTERISTICS:
 (A) LENGTH: 5
 (B) TYPE: amino acid
 (D) TOPOLOGY: linear (xi) SEQUENCE DESCRIPTION: SEQ ID NO:8:

Gly Phe Leu Gly Phe
                  5

(2) INFORMATION FOR SEQ ID NO:9:

(i) SEQUENCE CHARACTERISTICS:
 (A) LENGTH: 6
 (B) TYPE: amino acid
 (D) TOPOLOGY: linear (xi) SEQUENCE DESCRIPTION: SEQ ID NO:9:

Gly Gly Phe Leu Gly Phe
                      5

(2) INFORMATION FOR SEQ ID NO:10:

(i) SEQUENCE CHARACTERISTICS:
 (A) LENGTH: 27
 (B) TYPE: amino acid
 (D) TOPOLOGY: linear (xi) SEQUENCE DESCRIPTION: SEQ ID NO:10:

His Ser Asp Gly Thr Phe Thr Ser Glu Leu Ser Arg Leu Arg Asp
              5                  10                      15

Ser Ala Arg Leu Glu Arg Leu Leu Gln Gly Leu Val
                20              25

DRUG DELIVERY SYSTEM FOR THE SIMULTANEOUS DELIVERY OF DRUGS ACTIVATABLE BY ENZYMES AND LIGHT

FIELD OF THE INVENTION

This invention relates to treatment of neo-plastic diseases using polymeric drugs with increased therapeutic efficacy. These drugs are composed of a polymer combination with two or more different drugs attached, one of which is photoactivatable. By combination is meant either a mixture of two copolymers, one containing a photosensitizer (photoactivatable drug) and the other containing an antineo-plastic drug, or a single copolymer having a photosensitizer and an antineoplastic drug attached to the same polymer molecule. Such combinations are useful for the treatment of neoplastic diseases. The polymers may also contain a suitable targeting moiety. The photoactivatable drug may be bound to the polymeric carrier either by a nondegradable or by an enzymatically degradable bond. The antineoplastic drug is always bound to the polymeric carrier via bonds stable in the blood stream, but susceptible to cleavage by lysosomal enzymes. When so formulated, both drugs enter the same cells almost concurrently because the body distribution of both drugs will generally be the same. This is fundamentally different compared to the combination therapy of two low molecular weight drugs not attached to polymer chains because the body distribution of each drug is different. Moreover, after reaching the lysosomal compartment of the cell, the drug bound via an enzymatically degradable bond is released from the carrier by the action of lysosomal enzymes and diffuses through the lysosomal membrane into the cytoplasm. The photoactivatable drug, remains inactive in the cell. It becomes activated only after light of a suitable wavelength is applied (a laser or a chemiluminescence reaction or any other suitable source may be used as a light source). One of the main advantages of this approach is the optimization of the action of both drugs. The rate of release of the first anticancer agent (e.g. adriamycin) by lysosomal enzyme cleavage may be controlled by the structure of the side-chain, for example the oligopeptide sequence, P. Rejmanova et al., Makromol. Chem., 184, 2009(1983). After an optimal time period, light can be applied, resulting in the activation of the photoactivatable drug. This will cause the death of those cells which were not destroyed by the first anticancer drug.

The present invention minimizes the amount of cancer cells which are resistent to chemotherapy, thus decreasing substantially the possibility of tumor recurrence. This approach has a higher potential in the successful treatment of multidrug resistant cells (MDR) than the presently available therapies. The concentration of drugs in the cell, when this method is used, is increased, even if the transport of the drugs into the cell interior or MDR cells is impaired. If a suitable targeting moiety is attached (e.g. structures complementary to cell surface antigens or receptors), then a combined intracellular and extracellular action will increase the efficacy (the intracellular action will proceed by the above described mechanism, the extracellular action will be on the plasma membrane). The polymeric drug will bind to the cell surface receptor/antigen) of MDR cells and may not be internalized. However, after irradiation, the photoactivatable drug will produce singlet oxygen with consequent membrane damage, ultimately resulting in cell death.

BACKGROUND OF INVENTION

Many of the low molecular weight drugs used in chemotherapy rapidly enter all types of cells by random diffusion through the cell membrane. This lack of selectivity decreases their availability at the desired target tissue and sometimes causes undesirable side effects. Cellular uptake is rapid so that the therapeutic effect is not extended over a period of time. Furthermore, glomerular filtration can rapidly remove the drugs from the bloodstream.

The covalent attachment of low molecular weight bioactive molecules to soluble polymeric carriers prevents both glomerular filtration and cellular absorption by simple diffusion. Uptake is restricted to cells capable of a substrate selective mechanism known as pinocytosis, in which a region of the limiting membrane of the cell engulfs the macromolecule and is then detached inwards to form a free intracellular vesicle containing the captured material.

This difference in uptake mechanisms affords a potential method for directing drugs specifically to those cells where their therapeutic effect is required.

A further difference lies in the subsequent fates of the two types of molecule i.e, polymer bound or free drug. Small molecules which enter by diffusion tend to find their way to all parts of the cell, but macromolecules, following pinocytosis, are transported in their intracellular vesicles directly to the lysosomal compartment of the cell where an array of hydrolytic enzymes is available.

The pinocytic uptake of a polymeric drug in which the drug-carrier linkage is susceptible to lysosomal hydrolysis therefore affords a mechanism for the controlled intracellular release of a bioactive molecule leading to its appearance within the cytoplasm of the target cell. The theoretical considerations involved in the design of such a drug system have recently been reviewed in an article by J. Kopecek entitled "Synthesis of Tailor-made Soluble Polymeric Carriers" in *Recent Advances in Drug Delivery Systems* (Plenum Press, 1984).

In order to design such a system, two criteria must be satisfied. First, a drug-carrier linkage must be devised which undergoes controlled lysosomal hydrolysis, but is capable of withstanding the action of enzymes in the bloodstream. Second, the drug delivery system must be able to achieve specific uptake at those target cells where the therapeutic effect is required, with minimal uptake by other cells.

There are basically three forms of pinocytosis: fluid phase, adsorptive, and receptor-mediated. Fluid phase pinocytosis is the most general form in which soluble macromolecules and solutes enter the cell in liquid droplets. Many, if not all nucleated cells use fluid phase pinocytosis to internalize material from the extracellular space. It is known as a "constitutive" process because it is continuous (as opposed to triggered as is phagocytosis) in that the cell is always ingesting pieces of its plasma membrane.

Adsorptive pinocytosis is also a relatively indiscriminate process. However, in this case a macromolecule may physically adsorb (nonspecifically) to a site on the cell membrane, and then by the invagination process be taken in by the cell.

Receptor-mediated pinocytosis is by far the most specific form of pinocytosis by which a macromolecule with a marker complementary to a cell surface receptor binds to that receptor and is subsequently internalized to the cell interior. In this way, macromolecules such as hormones, transport proteins, proteins modified for degradation, growth factors, and some antibodies are taken in by cells from the extracellular fluid. The advantage of receptor-mediated pinocytosis lies in the fact that a higher concentration of ligand may be internalized in specific cells than by the other mechanism.

Regardless of the mode, once internalized by pinocytosis, the ultimate leading fate of a solute is delivery to secondary lysosomes where it can be degraded and distributed by cell in various ways. Naturally, since during the process of fluid phase pinocytosis there is indiscriminate uptake of cell surface markers, the cell is equipped with the machinery to recycle essential lipids and proteins back to the cell membrane.

Although the process of pinocytosis affords a degree of selectivity towards macromolecules, a selectivity which can be optimized, e.g., by varying the molecular weight, greater target selectivity can be achieved by the incorporation within the macromolecule of a specific "targeting moiety". Cells possess specific receptors and cell antigens on their surfaces which "recognize" and interact with certain types of molecular entities known as specific determinants. High cell specificity can be achieved by the incorporation in the polymeric drug of a determinant which is recognized by the type of cells in which the therapeutic effect is required.

Thus, a drug delivery system which would allow specific targeting followed by intracellular drug release requires the following features:
  (a) an inert polymeric carrier, which is preferably susceptible to lysosomal hydrolysis to facilitate elimination of the polymer from the body,
  (b) a degradable drug-carrier linkage which is resistant to extracellular hydrolysis, but which is subject to controlled lysosomal hydrolysis, and
  (c) an optional targeting moiety if desired.

Although natural macromolecules have been used as carriers, synthetic polymers offer the advantages that the molecular weight can be more readily adjusted for optimum cell selectivity and, unlike many natural macromolecules, they are not immunogenic. They also lend themselves more readily to commercial production.

Synthetic polymers based on N-(2-hydroxypropyl)-methacrylamide (HPMA) have been proposed as potential drug carriers, see U.S. Pat. Nos. 4,062,831 and 4,097,470; such polymers are soluble in aqueous media and have good biocompatibility. Furthermore, by the incorporation of p-nitrophenylesters of N-methacryloyl oligopeptides they can be combined with many drugs which contain a primary amino group. The polymeric chains may be cross-linked to a level below the gel point in order to achieve the optimum molecular weight and to provide, by the use of biodegradable cross-linkages, a means of degrading the polymer to facilitate elimination from the body.

Since lysosomal enzymes include a number of proteinases with the ability to hydrolyse peptide linkages, direct linkage of the bioactive molecule to the polymer chain by an amide bond would appear to have the potential for lysosomal hydrolysis. In practice, this is not found to be the case. However, peptide "spacers" interposed between the drug and the carrier have been found to undergo degradation by lysosomal enzymes within a broad range of rates. The bond actually cleaved is usually that between the drug and the neighboring amino acid, although this is not always the case. The rate of hydrolysis, that is the rate of drug release, is found to depend greatly on the number and the nature of the amino acid residues in the peptide spacer. Spacers of less than two amino acids are not generally susceptible to lysosomal hydrolysis. Peptide spacers designed to match the known substrate specificity of thiol-proteinases, known to be present in lysosomes, are particularly effectively cleaved.

It has been demonstrated that the modification of glycoproteins to give oligosaccharide side-chains which terminate in galactose leads to a dramatic increase in the deposition of the glycoproteins in the parenchymal cells of the liver. The galactose moiety acts as a specific determinant interacting with receptors localized on the plasma membrane of the liver cells. This offers a potential mechanism for the targeting of drugs to hepatoma, a particularly difficult cancer to treat. Furthermore, galactosamine bound to HPMA copolymers by an amide bond gives a similar result, indicating that receptors on hepatocyte membranes recognize the galactose moiety not only in glycosides, but also when present as N-acyl galactosamine. A number of other recognition systems are known, for example, the N-acetylglucosamine/mannose recognition system of Kupffer cells and macrophages and the phosphohexose recognition system of fibroblasts.

Another possible targeting mechanism is to bind the polymeric drug to an antibody which is recognized specifically by those cells which have the appropriate antigenic receptors. Drug molecules have been bound directly to immunoglobulins, but this can lead to loss of drug activity, loss of antibody activity and/or solubility of the conjugate.

A further targeting mechanism is to include a protein or a hormone, for example transferrin and melanocyte-stimulating hormone, which will bind specifically to the target cell type.

While the desirability of synthesizing targeted polymeric drugs with hydrolyzable peptide spacers has been referred to in the prior art (see Kopecek, supra), the identification of peptide spacers which are capable of controlled intracellular drug release at a satisfactory rate and the identification of linking group/determinant combinations which give good targeting to the desired cell receptors, are matters of continuing research.

As discussed earlier, the rate of lysosomal hydrolysis of a peptide spacer is dependent on both the number and the nature of the amino acid residues. This is a reflection of both steric and structural factors. Thus the rate of terminal hydrolysis of a spacer containing 2 to 4 amino acid residues is generally dependent on the number of residues present, an effect attributed to stearic interaction between the polymer chain and the enzyme.

For a given length of peptide, the rate of hydrolysis is dependent on the nature (and sequence) of the amino acid residues. This dependency arises from the substrate specific nature of the lysosomal enzymes responsible for cleavage of the peptide spacer. The region of the enzyme where interaction with the substrate takes place is known as the "active site" of the enzyme. The active site performs the dual role of binding the substrate while catalyzing the reaction, for example cleavage. Studies of the structures of the complexes of proteolytic enzymes with peptides indicate that the active site of these enzymes is relatively large and binds to several amino acid residues in the peptide.

Thus the degradability of a particular bond in a peptide chain depends not only on the nature of the structure near the cleaved bond, but also on the nature of the amino acid residues which are relatively remote from the cleaved bond, but play an important part in holding the enzyme in position during hydrolysis. So far the detailed structures of the active sites of lysosomal enzymes have not been determined and this has proved to be an obstacle to the preparation of peptide spacers which undergo lysosomal hydrolysis at a suitable rate for use in polymer drugs.

DESCRIPTION OF PRIOR ART

U.S. Pat. No. 5,037,883 issued Aug. 6, 1991, (Kopecek et al.) describes a drug conjugate of an inert polymeric carrier attached through a peptide linkage to bio-active molecules. The conjugates also contain a targeting mechanism such as an antibody, monosaccharide, disaccharide, or a protein. This patent teaches that copolymers of N-(2-hydroxypropyl)methacrylamide containing oligopeptide sequences terminated in anticancer drugs (e.g. adriamycin, daunomycin, melphalan) and bound to targeting moieties (e.g. galactosamine, fucosylamine, anti-Thy 1.2 antibodies, anti-Ia antibodies) have a higher therapeutic efficacy compared to the low molecular weight drugs that contain no polymers. In particular a conjugate containing adriamycin as a drug (bound via a Gly-Phe-Leu-Gly oligopeptide sequence) and galactosamine as a targeting moiety is described. The patent is limited in scope to polymers containing a single bioactive moiety and a targeting moiety..

J. D. Spikes, *The Science of Photobiology*, 2nd Edition, K. C. Smith, ed., Plenum Press, N.Y., 1988, pp 79–110, describes photosensitizers that are activated with light of a characteristic wavelength, ultimately resulting in the formation of singlet oxygen, a highly reactive specie. The mechanism of photosensitized reactions has been exploited for use in cancer therapy. Photodynamic Therapy (PDT) is the term coined for using a photosensitizer plus light in the destruction of cancer cells. An advantage of using therapy of this type is that the photosensitizer remains inert until its activation with light. One such sensitizer, hematoporphyrin derivative (HPD), a porphyrin, has been studied extensively due to its inherent ability to localize in tumor tissue, J. Moan, Photochem. Photobiol., 43, 681 (1986). But, there is still the potential for nonspecific uptake in normal cells. This poses the problem of ultrasensitivity in which patients can remain sensitive even to daylight for up to thirty days following PDT treatment, T. J. Dougherty, J. Invest. Derm., 77, 122(1981). Therefore, it is desired to target photosensitizers with monoclonal antibodies. This has been demonstrated by coupling HPD to monoclonal antibodies against DDBA/2J myosarcoma M-1 cells, D. Mew et al., J. Immunol., 130, 1473(1983). But, many photosensitizers are extremely hydrophobic molecules which upon binding can alter antibody solubility (R. Arnon et al., Cancer Surv., 1, 429(1982) and decrease antibody activity, B. Rihova et al., Makromol. Chem. Suppl., 9, 13(1985). A water soluble polymeric carrier (Dextran) was coupled with monoclonal anti-T cell (anti-Leu-1) antibodies to target a photosensitizer (chlorin $e_6$) to HPB-ALL human T leukemia cells in vitro, A. Oseroff et al., Proc. Natl. Acad. Sci. USA, 83, 8744(1986). Photosensitizers have been attached to polymers and used in drug therapy for the destruction of a variety of cancer cells, J. Kopecek et al. Journal of Controlled Release, 16, 137–144(1991); N. L. Krinick et al., SPIE Advances in Photochemotherapy, 997, 70–83(1988); and N. L. Krinick et al., Makromol. Chem., 191, 839–856(1990).

None of these references suggest the concurrent administration of a combination of anticancer drugs and photosensitizers attached to polymeric carriers as used in the present invention.

OBJECTS AND BRIEF SUMMARY OF THE INVENTION

It is an object of the present invention is to provide soluble bioactive copolymers containing a pendant chemotherapeutic agent and pendant photosensitizers attached via enzymatically degradable bonds.

A further object of this invention is to provide soluble bioactive copolymers containing a pendant chemotherapeutic agent and a pendant photosensitizer and also a pendant determinant attached by enzymatically degradable bonds.

It is also an object of this invention to provide soluble bioactive copolymers containing pendant photosensitizer molecules attached by either nondegradable or enzymatically degradable bonds and a chemotherapeutic agent attached by degradable bonds.

A still further object of this invention is provide a method for the treatment of neo-plastic diseases by the administration of soluble bioactive copolymers containing a pendant chemotherapeutic agent and pendant photosensitizers attached via enzymatically degradable bonds. The copolymer may also contain a determinant or targeting moiety.

A still additional object of this invention is to provide a method for the treatment of neo-plastic diseases by the administration of a combination of copolymers, one containing a pendant chemotherapeutic agent and the other containing a pendant photosensitizer wherein each copolymer contains the same targeting moiety.

Another object of this invention is to provide a method for the treatment of neo-plastic diseases by the administration of copolymers containing pendant photosensitizer molecules attached by either nondegradable or enzymatically degradable bonds and chemotherapeutic agents attached by degradable bonds.

Yet another object is to provide soluble bioactive copolymers containing a pendant chemotherapeutic agent and pendant photosensitizers attached via enzymatically degradable bonds with a targeting moiety specific for a tumor marker on the cancer cell.

An additional object of is to provide soluble bioactive copolymers containing pendant photosensitizer molecules attached by either nondegradable or enzymatically degradable bonds and chemotherapeutic agents attached by degradable bonds with a targeting moiety specific for a tumor marker on the cancer cell.

A further additional object of this invention is to provide a method for the treatment of neo-plastic diseases by the administration of copolymers containing a pendant chemotherapeutic agent and pendant photosensitizers attached via enzymatically degradable bonds with a targeting moiety specific for a tumor marker on the cancer cell.

A yet further additional object of this invention is to provide a method for the treatment of neo-plastic diseases by the administration of copolymers containing pendant photosensitizer molecules attached by either nondegradable or enzymatically degradable bonds and chemotherapeutic agents attached by degradable bonds with a targeting moiety specific for a tumor marker on the cancer cell.

These and other objects may be obtained by administration of "combination" copolymers, containing a chemotherapeutic agent and a photosensitizer, for the treatment of tumors. Two separate copolymers, one containing a chemotherapeutic agent and the other containing a photosensitizer, have been found to be superior, when administered at the same time, to the administration of each polymer administered separately in treating neoplastic diseases. Also, a single copolymer containing both a chemotherapeutic agent and a photosensitizer can be utilized instead of a mixture of copolymers. The specificity of these copolymers may be improved by the attachment of a targeting moiety to each polymer molecule. However, experiments with the present invention demonstrate that the use of polymeric carriers containing both an anticancer drug and a photosensitizer results in a greater quantity of polymer bound drug accumulating in the tumor than does the free drug even without the incorporation of a targeting moiety.

These polymeric macromolecules enter targeted cells by pinocytosis; binding low molecular weight drugs to copolymers alters their manner of uptake from diffusion to pinocytosis which may reduce the side effects normally elicited by the free drugs. For this reason it is possible to use much lower doses of both drugs when attached to the "combination" copolymer. The use of either two separate copolymers, one containing a photosensitizer and the other containing an anticancer drug, or the same copolymer having both an anticancer and photosensitizer attached, is superior in the treatment of neo-plastic diseases using a single copolymer containing only an anticancer or photosensitizer attached since a lower dose can be used. In addition, it is possible to use even lower doses if the two drugs have a synergistic anticancer effect. Attaching both drugs to the same copolymer ensures that both drugs will enter the same cell at the same time. A targeting moiety specific for a tumor marker on the cancer cell also bound to the "combination" copolymer side chains will facilitate or enhance the direction of the copolymer containing both drugs specifically to the targeted cancer cells.

A time lag, after administration, should be allowed for optimal uptake of these copolymers in the tumor tissue compared to surrounding normal tissue, for the anticancer agent to begin to take effect. Then laser light or other light sources of the appropriate wavelength and energy are applied, exciting the photosensitizer to its first excited singlet state. Intersystem crossing causes the conversion of the singlet state sensitizer into its corresponding triplet state. Energy transfer from the triplet state sensitizer to ground state molecular oxygen causes the production of singlet excited oxygen. The singlet oxygen produced attacks the lysosomal membrane of the cell thereby releasing lysosomal enzymes into the cytosol with the consequence of cell death. The effect of the anticancer agent eliminates cells which the photosensitizer did not destroy. The tumor recurrence is greatly decreased by the use of the above described therapy.

The antitumor efficacy of the combination copolymers (such as HPMA copolymers), containing an anticancer drug (such as adriamycin) and containing a photosensitizer (such as meso-chlorin $e_6$ monoethylene diamine disodium salt ($ce_6$)) in vivo was found to be superior to the use of copolymers containing the photosensitizer and polymers containing the anti-cancer drug administered alone. The adriamycin is active only once it is enzymatically released from the copolymer and the $ce_6$ is activated with light and elicits photodynamic effect in vivo whether or not it remains bound to the copolymer. An anticancer drug enhances PDT treatment (and vice versa) because long term cure of solid tumors is difficult to achieve with PDT. On the other hand, chemotherapeutic agents have their own share of problems including multidrug resistance and other toxic side effects. The present invention reduces side effects because lower doses of copolymers are required.

DETAILED DESCRIPTION OF INVENTION

The main comonomer unit determines the properties of the polymeric carriers. Several comonomer units may be used resulting in water soluble copolymers. Functionally, any inert copolymer to which appropriate spacers may be attached for binding the bioactive and-/or targeting moiety may be utilized. The copolymer is usually made by copolymerization of the desired mole ratio of underivatized comonomer units with the desired ratio of comonomer units which have been derivatized to contain appropriate attachment groupings or spacers, which, in turn, possess reactive groupings to which bioactive agents or targeting moieties may be subsequently attached. Typical comonomer units may be made of N-(2-hydroxypropyl)methacrylamide (HPMA), N-methylacrylamide, and N,N-dialkylacrylamides. Other suitable carries include polyamino acids, polysaccharides, copolymers containing polyethyleneoxide sequences, polyvinyl pyrrolidone-maleic anhydride copolymers, and the like.

Typically, the initial step involves the preparation of a polymer precursor. In the case of synthetic copolymers, the initial step generally involves the copolymerization of the underivatized and derivatized comonomer units to provide a copolymeric precursor in which the derivatized comonomer units contain the attachment or spacer groupings having leaving groups (e.g. p-nitrophenoxy groups) for subsequent addition of the bioactive drugs or targeting moieties. In the case of other polymers, such as polysaccharides, (e.g. dextran and the like) and Polyamines, the step is one of activation wherein activating agents (e.g. p-nitrophenoxy groups) are attached to the polymer chain. The second step involves the addition of the bioactive agents and/or targeting moieties to the precursor polymer or copolymer.

From the above, it is evident that the term "copolymer" is to be broadly interpreted to include any suitable polymer chain wherein the repeating monomer units making up the chain may be the same but which may have different pendant groups attached to the monomer unit through a spacer. Thus, an HPMA copolymer will be synthesized from underivatized HPMA and N-methacryloylated peptides containing active p-nitrophenoxy groupings. On the other hand, a polysaccharide copolymer will contain saccharide units which are not substituted by any derivatives and other saccharide units which have been activated by the attachment of a reactive group such as a p-nitrophenoxy moiety. The copolymers are water soluble and will generally have a molecular weight, inclusive of the weight of the anticancer drug, photoactivatable drug, and determinant, in the range of between about 10,000 and 50,000.

As stated in U.S. Pat. No. 5,037,883 about 5.0 to 99.7 mol % of the polymeric units are underivatized comonomer units with HPMA being the preferred comonomer.

A certain amount (percentage) of the comonomer units necessarily contain enzyme cleavable side chains terminating in an anticancer drug. These side chains permit site-specific release of the anticancer drug in the lysosomal compartment of the cell. These comonomer units can vary between about 0.2 to 20.0 mol % of the units making up the copolymer. The structure of the side-chains must be tailor-made so as to be stable in the blood stream, yet susceptible to hydrolysis by lysosomal enzymes intracellularly. Oligopeptide sequences, oligosaccharide sequences or structures similar to those in nucleic acids also may be used as points of drug attachment. Since the preferred copolymer is HPMA, preferably these units will be N-methacryloylated peptides to which the drug is attached. The linkages or peptide spacers can be any of those mentioned in U.S. Pat. No. 5,037,883 and are selected from the group consisting of Gly-Gly, Gly-Phe-Gly, Gly-Phe-Phe, Gly-Leu-Gly, Gly-Val-Ala, Gly-Phe-Ala, Gly-Leu-Phe, Gly-Leu-Ala, Ala-Val-Ala, Gly-Phe-Leu-Gly (SEQ ID NO:1), Gly-Phe-Phe-Leu (SEQ ID NO:2), Gly-Leu-Leu-Gly (SEQ ID NO:3), Gly-Phe-Tyr-Ala (SEQ ID NO:4), Gly-Phe-Gly-Phe (SEQ ID NO:5), Ala-Gly-Val-Phe (SEQ ID NO:6), Gly-Phe-Phe-Gly (SEQ ID NO:7), Gly-Phe-Leu-Gly-Phe (SEQ ID NO:8), or Gly-Gly-Phe-Leu-Gly-Phe (SEQ ID NO:9). Particularly preferred as a peptide spacer is Gly-Phe-Leu-Gly (SEQ ID NO:1). This spacer will be repeatedly referred to throughout the specification and claims either as Gly-Phe-Leu-Gly or (SEQ ID NO:1) which terms can be used interchangeably.

Suitable anticancer drugs for attachment to the peptide linkages are inclusive of, but not limited to, adriamycin, daunomycin, melphalan and bleomycin.

The same comonomer units, containing degradable side-chains terminated in a photoactivatable drug may be used. The concentration range of these comonomer units in the polymer will be the same as for the anticancer drugs. However, that does not mean that the anticancer drug and the photoactivatable drug will always be present as a 1:1 molar ratio. It may be that the ratio of these drugs within the combination polymer will vary according to the patient, the type of cancer being treated, the tissue sites or any other variable which may be affected by the presence of these bioactive agents. Also, the comonomer units may contain nondegradable side-chains terminated in a photoactivatable drug. Such non-degradable side-chain spacers may include amino acids such as glycine, or $\epsilon$-aminocaproic acid.

The photoactivatable drug or photosensitizer can be made up of porphyrins, phthalocyanines, purpurins, chlorins, napthalocyanines, cationic dyes, tetracyclines, and the like.

Each copolymer may also contain a targeting moiety. Both nondegradable and enzymatically degradable side-chains may be used with the targeting moiety. The content of this comonomers to which targeting moieties can be attached will vary between 0 and 94.8 mol %. Again, with reference to U.S. Pat. No. 5,037,883, when a targeting moiety is present, the copolymer will contain between about 0.1 to 94.8 mol % of units capable of binding a targeting moiety. Since the preferred copolymer is HPMA, the comonomer will be derived from a member selected from the group consisting of N-methacrylamide, N-methacrylic acid or an N-methacryloylated amino acid or peptide. When present, the enzymatically degradable side chains are preferably amino acid or peptide moieties selected from the group consisting of Leu, Phe, Gly-Gly, Gly-Leu-Gly, Gly-Val-Ala, Gly-Phe-Ala, Gly-Leu-Phe, Gly-Leu-Ala, Ala-Val-Ala, Gly-Phe-Leu-Gly (SEQ ID NO:1), Gly-Phe-Phe-Leu (SEQ ID NO:2), Gly-Leu-Leu-Gly (SEQ ID NO:3), Gly-Phe-Tyr-Ala (SEQ ID NO:4), Gly-Phe-Gly-Phe (SEQ ID NO:5), Ala-Gly-Val-Phe (SEQ ID NO:6), Gly-Phe-Phe-Gly (SEQ ID NO:7), Gly-Phe-Leu-Gly-Phe (SEQ ID NO:8), or Gly-Gly-Phe-Leu-Gly-Phe (SEQ ID NO:9) with Gly-Phe-Leu-Gly (SEQ ID NO:1) again being most preferable.

As targeting moieties, structures complementary to cell surface antigens or receptors may be used. Such are inclusive of saccharides, e.g. galactosamine, fucosylamine, lactose; hormones, e.g. MSH, secretin; opiates; monoclonal and polyclonal antibodies.

The photoactivatable drugs are susceptible to activation by light sources such as from lasers and fiber optic systems presently used in PDT, chemiluminensence systems and the like. The chemiluminescence activator may be administered directly in the area of tumor localization, or may also be targetable, at least in part, to the tumor site using a polymeric delivery system similar to that disclosed above. Peroxide formation needed to activate a chemiluminescence system may be produced as a result of an enzymatic reaction (e.g. delivery of an enzyme such as glucose oxidase to a cell membrane which reacts with glucose resulting in the formation of hydrogen peroxide) or by a chain autoxidation reaction by the photosensitizer itself initiated by pulsed light. In the latter case, a cyclic reaction may result with a sort of synergistic mechanism.

While the invention has been defined in its broader aspects above, the following is a description of a preferred embodiment wherein the copolymer units are based on HPMA. However, one skilled in the art will be able to utilize other copolymer units to provide other copolymeric molecules containing the same pendant side chains terminating in anticancer drugs, photoactivatable drugs and targeting moieties.

The copolymers utilized in this invention are synthesized by conventional means and are depicted by the following abbreviated formulae:

P-Gly-Phe-Leu-Gly-adria (Copolymer I)

where P stands for a copolymeric carrier as will be more completely defined hereinafter and adria stands for the anticancer drug adriamycin as will also be more completely defined hereinafter.

P-Gly-Phe-Leu-Gly-ce$_6$ (Copolymer II)

were P is as defined above and ce$_6$ is a photoactivatable drug mesochlorin e$_6$.

P-Gly-ce$_6$ (Copolymer III)

where P is as defined above and ce$_6$ is meso-chlorin e$_6$.

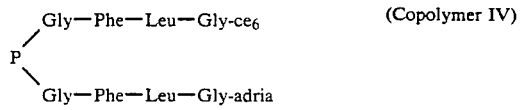

(Copolymer IV)

where P, ce$_6$ and adria are as defined above.

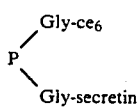
(Copolymer V)

where P and ce₆ are as defined above and secretin is a polypeptide determinant having a 27 amino acid chain length.

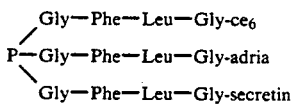
(Copolymer VI)

where P, ce₆, adria and secretin are as defined above.

As previously stated, HPMA is the preferred comonomer unit. Using this comonomer, in derivatized and underivatized form, a more detailed structure of each of Copolymers I–IV follows wherein x, y, z and w are expressed in terms representing the mol % of each unit in the copolymer. Thus, x is an integer representing between about 5.0 to 99.7 mol %; y is an integer representing between about 0.3 to 20.0 mol; %; z is an integer representing between about 0.2 to 20.0 mol % and w is an integer representing between about 0.1 to 25.0 mol %.

Individual Copolymers

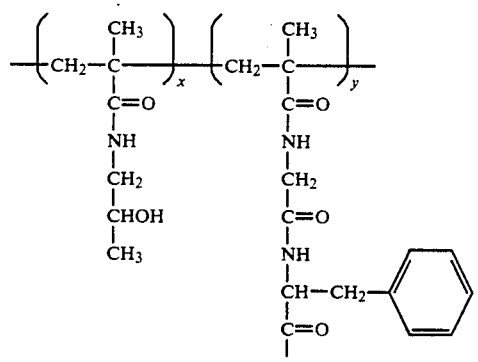

P-G-F-L-G-adria
(Copolymer I)

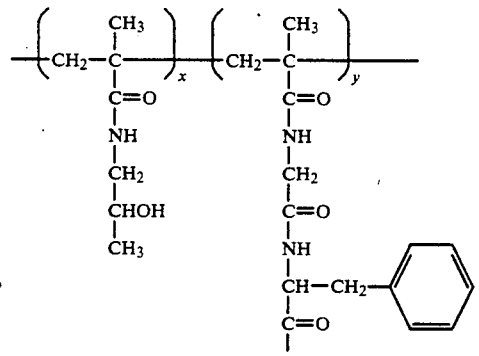

P-G-F-L-G-c8₆
(Copolymer II)

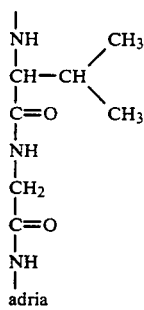

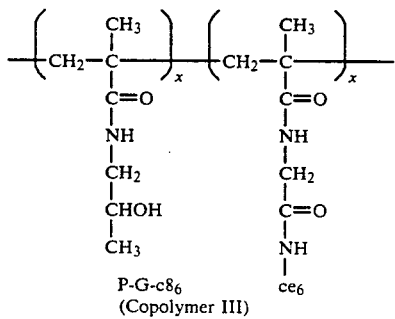

P-G-c8₆
(Copolymer III)

Combination Copolymer

-continued
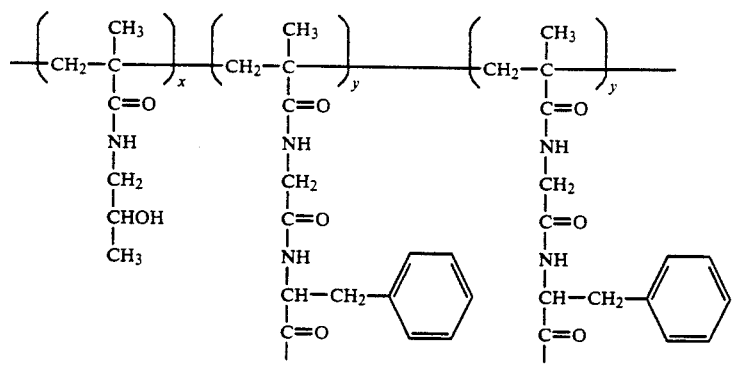
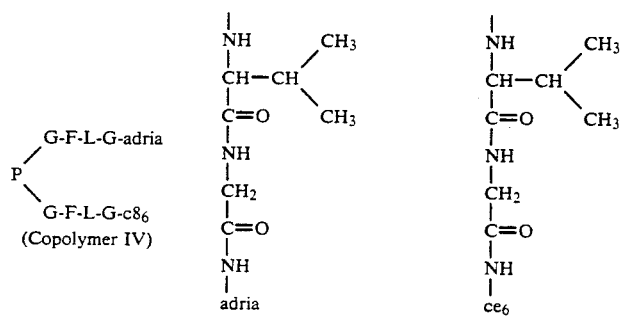
(Copolymer IV)
Targeted Copolymer
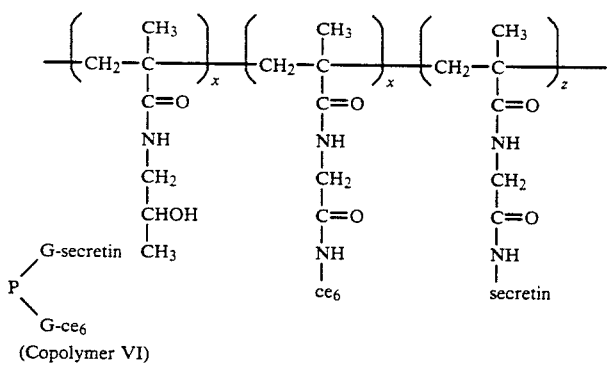
(Copolymer VI)
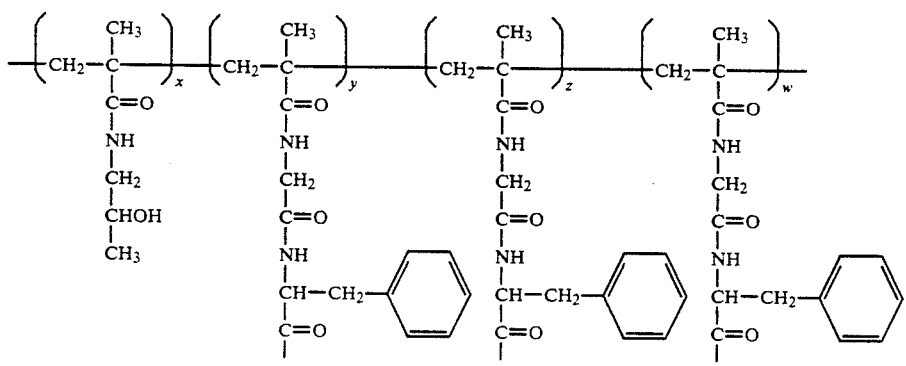

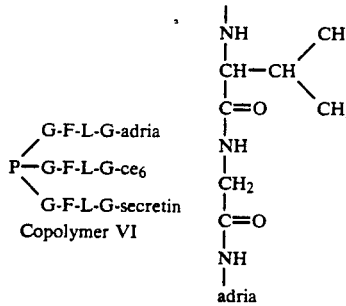
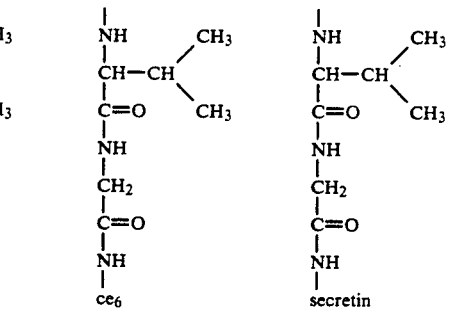

The synthesis of monomers utilized to prepare copolymer precursors for the synthesis of Copolymers I through VI is given in Examples 1-4 which follow:

Example 1

N-(2-Hydroxypropyl)methacrylamide (HPMA)

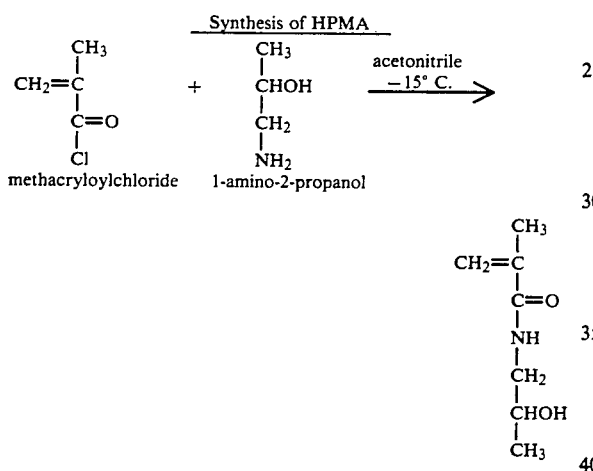

As illustrated by the above reaction sequence, the HPMA monomer (following the method of J. Strohalm et al., Angew. Makromol. Chem., 70, 109(1978).) was prepared by dissolving 229.7 ml (223.5 g, 2.98 moles) of 1-amino-2-propanol in 550 ml acetonitrile. Octylpyrocatechin inhibitor was added and the solution was cooled to $-20°$ C. Next, 153 ml metacryloyl chloride (163.7 g, 1.57 moles) was dissolved in 350 ml acetonitrile. The methacryloylchloride solution was slowly dropped into the 1-amino-2-propanol solution under vigorous stirring with care to keep the temperature at $-15°$ C. After addition, the temperature of the mixture was allowed to rise to $20°$ C. The 1-amino-2-propanol.HCl byproduct was quickly filtered off with a course filter. The flask was scraped after the first crystals formed and crystallization of the filtrate continued at $-30°$ to $-45°$ C. The crystals were filtered off rapidly. The HPMA was recrystallized in a mixture of MeOH/ether 1:3 (dissolved under warm tap water) and then recrystallized in acetone to remove any polymer formed. The main product (64.4 g) melted at $70°-71°$ C.

Example 2

Methacryloylglycine p-Nitrophenyl Ester (MA-Gly-ONp or MA-G-ONp) Intermediate MA-Gly Preparation:

Methacryloylglycine (MA-Gly or MA-G), the precursor of MA-Gly-ONp, was synthesized according to the following reaction scheme.

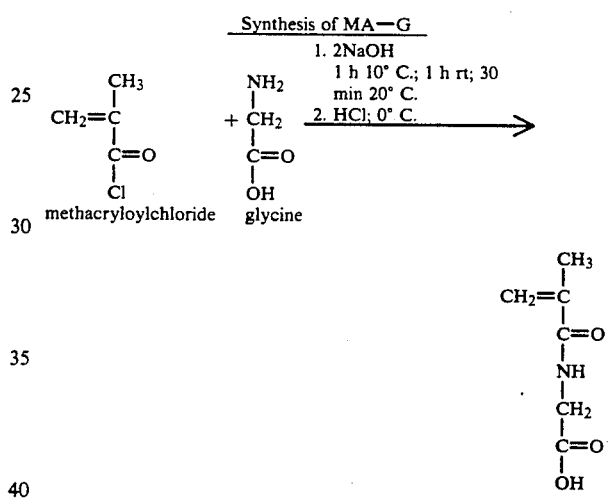

Thirty grams of glycine (0.3996 moles) were dissolved in 100 ml of 4N NaOH and hydroquinone inhibitor was added. The mixture was cooled to $0°$ C. Methacryloylchloride (38.7 ml, 0.3996 moles) and 99.8 ml 4N NaOH were slowly dropped into the glycine solution simultaneously. The reaction proceeded for 1 h at $10°$ C. The pH was adjusted to 9.5 with 4N NaOH. The reaction continued for 1 h at room temperature and then 30 min in a $20°$ C. water bath. The reaction mixture was cooled to $0°$ C. and approximately 65 ml 1:1 HCl:H$_2$O was slowly added dropwise until the pH reached 2-3. The mixture was extracted 2 times with ethylacetate (more H$_2$O was added to the water layer to dissolve the salts formed). The solution was dried with sodium sulfate for 1 h and filtered. The volume was reduced to about 450-500 ml and approximately 10 ml hexane was added. The mixture was refrigerated overnight and the methacryloylglycine crystals were isolated. The mother liquid was recrystallized in EtOH/hexane. The yield of these two products were 13.2 g and 6.5 g, respectively, both with melting points of $108°-109°$ C.

Methacryloylglycine p-Nitrophenyl Ester (MA-Gly-ONp) Preparation:

Using the above prepared MA-Gly, MA-Gly-ONp (NM-G-ONp) was synthesized according to the following sequence:

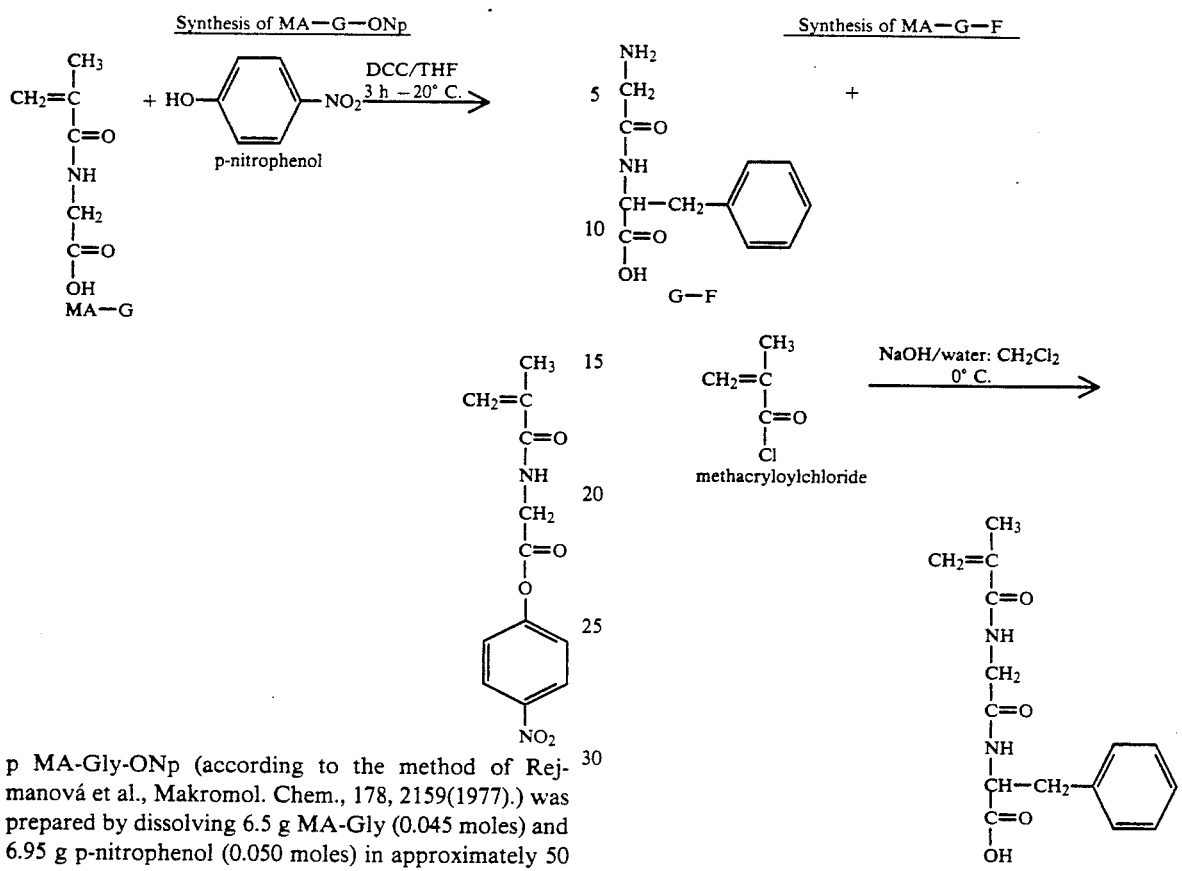

p MA-Gly-ONp (according to the method of Rejmanová et al., Makromol. Chem., 178, 2159(1977).) was prepared by dissolving 6.5 g MA-Gly (0.045 moles) and 6.95 g p-nitrophenol (0.050 moles) in approximately 50 ml THF. This mixture was cooled to −20° C. and then 10.31 g (0.05 mole) of dicyclohexylcarbodiimide (DCC) dissolved in 9.7 ml THF was dropped in slowly maintaining temperature at −20° C. The reaction continued overnight at 4° C. The next morning, the mixture was stirred for 3 h at room temperature. A few drops of acetic acid were added to terminate the reaction and the mixture was stirred for 30 minutes more at room temperature. The dicyclohexyl urea (DCU) byproduct formed was filtered off and washed with THF. The filtrate was evaporated to dryness and then dissolved in ethylacetate. The remaining DCU was filtered off. This last step was repeated. The product was dissolved again in ethylacetate and refrigerated overnight. The mixture was filtered one more time and evaporated to dryness. It was then crystallized overnight in the freezer in EtOH/ether. The crystals were filtered and washed with cold ether and then desiccated. The yield of the main product was 4.69 g and the melting point was 103°-104° C. The molar extinction coefficient was determined spectrophotometrically: $\epsilon_{272} = 10^4$ l/mole.cm (methanol).

Example 3

Methacryloylglycylphenylalanine p-Nitrophenyl Ester (MA-Gly-Phe-ONp or MA-G-F-ONp) Intermediate MA-Gly-Phe (MA-G-F) Preparation:

Methacryloylglycylphenylalanine (MA-Gly-Phe or MA-G-F), the precursor of MA-Gly-Phe-ONp, was synthesized according to the following reaction scheme.

Fifteen grams of glycylphenylalanine (Gly-Phe) (0.068 moles) were dissolved in a solution of 2.72 g (0.68 moles) NaOH in 60 ml $H_2O$. Octylpyrocatechin inhibitor was added and the mixture was cooled to 0° C. Under vigorous stirring a mixture of 7.76 g (7.2 ml, 0.074 mole) methacryloylchloride in 25 ml methylene chloride with added inhibitor and a solution of 2.98 g (0.024 moles) NaOH dissolved in 60 ml $H_2O$ were simultaneously dropped into the Gly-Phe solution slowly. Initially, more of the methacryloylchloride solution was added, and then they were added at the same rate. The pH was checked at 30 min (pH 6) and it was necessary to add 0.3 g more NaOH until pH 8-9 was reached. The reaction was complete when the water layer had a constant pH (mild alkaline) at which time the mixture was stirred an additional 30 minutes. The top layer was collected and the methylene chloride layer was extracted with water (10 ml). Tho water solutions were combined and 100 ml ethylacetate with inhibitor were added and the mixture was cooled to <20° C. Thirty-six percent HCl diluted with water 1:1 was added until pH 2-3 was reached (6-7 ml). The solution was quickly extracted with ethyl acetate. The ethyl acetate layer was collected and the water layer was washed 3 times with ethyl acetate. The solution was dried with sodium sulfate, filtered, and the crystals were washed with ethyl acetate. The solution was reduced to approximately 100 ml and refrigerated overnight. The crystals were filtered and washed with cold ether and desiccated. The main yield was 7.63 g and the product from the mother liquid was 7.26 g MA-Gly-Phe with a melting point of 141°-142.5° C.

Methacryloylglycylehenylalanine p-Nitrophenol Ester (MA-Gly-Phe-ONp Preparation:

Using the above prepared MA-Gly-Phe, MA-Gly-Phe-ONp (NM-G-F-ONp) was synthesized in a manner similar to MA-Gly-ONp according to the following sequence:

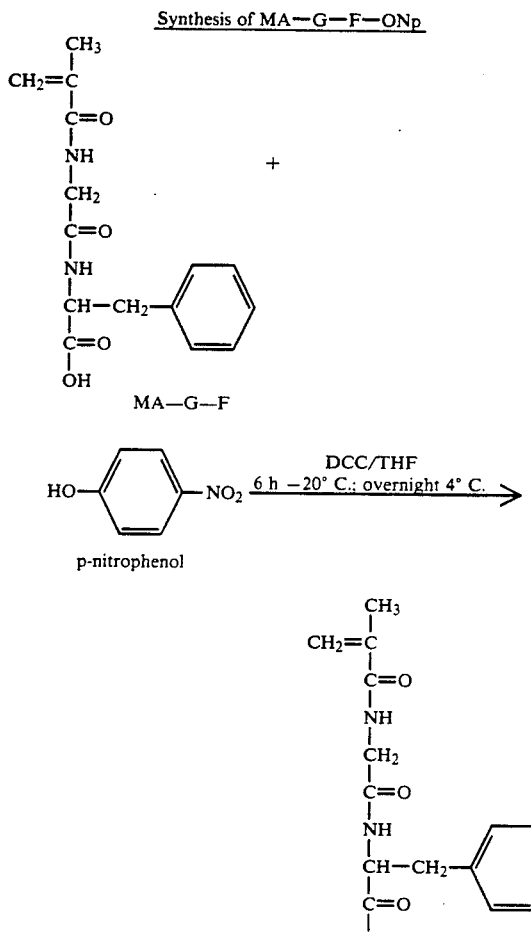

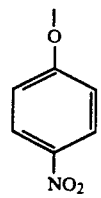

MA-Gly-Phe (7.63 g, 0.026 moles) and 4.02 g (0.029 moles) p-nitrophenol were dissolved in approximately 105 ml THF at room temperature. The mixture was cooled to −20° C. Under stirring, a solution of 5.96 g (0.029 moles) DCC in 15 ml THF was slowly dropped. The reaction proceeded for 6 hours at −20° C. and overnight at 4° C. The next day the solution was stirred for 1 hour at room temperature. A few drops of acetic acid were added and the stirring continued for 30 minutes more. The DCU was filtered off and washed with THF. The remaining solution was evaporated to dryness and then crystallized with EtOH/H$_2$O in the freezer overnight. The main product weighed 1.48 g (total yield of consecutive crystallization 3.1 g). The purified product had a molar extinction coefficient $\epsilon_{271} = 10^4$ l/mole.cm (DMSO) determined spectrophotometrically.

Example 4

Methacryloylglycylphenylalanylleucylglycine p-Nitrophenyl Ester (MA-Gly-Phe-Leu-Gly-ONp or MA-G-F-L-G-ONp) Intermediate MA-Gly-Phe-Leu-Gly (MA-G-F-L-G) Preparation:

Methacryloylglycylphenylalanylleucylglycine (MA-Gly-Phe-Leu-Gly or MA-G-F-L-G), the precursor of MA-Gly-Phe-Leu-Gly-ONp, was synthesized according to the following reaction scheme.

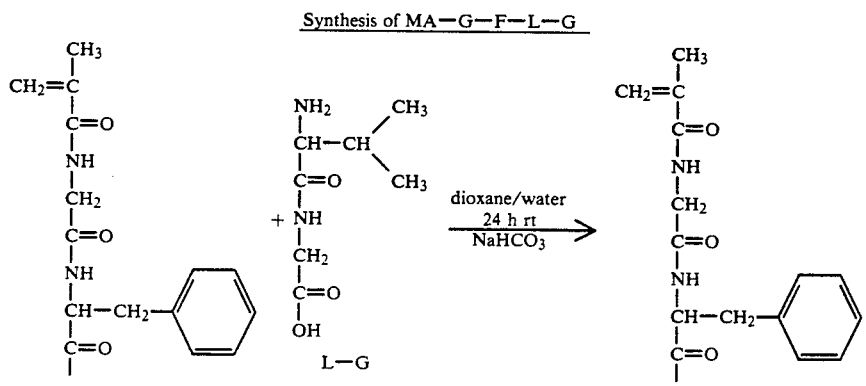

-continued
Synthesis of MA—G—F—L—G

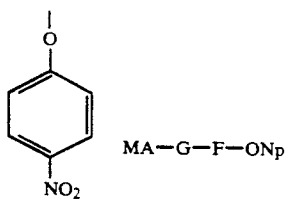
MA—G—F—ONp

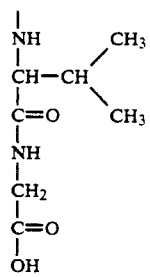

MA-Gly-Phe-ONp (0.5 g, $1.22 \times 10^{-3}$ moles) was dissolved in 7.35 ml dioxane with octylpyrocatechin inhibitor under warm tap water. Leu-Gly (0.25 g, $1.34 \times 10^{-3}$ moles) and 0.225 g ($2.68 \times 10^{-3}$ moles) $NaHCO_3$ were dissolved in 6 ml $H_2O$. Hydroquinone inhibitor was added to this mixture. The aqueous mixture was poured into the organic mixture and the reaction proceeded 24 hours at room temperature. The dioxane was removed by rotoevaporation ($<40°$ C.). The remaining product was cooled to $0°$ C. at which time approximately 5 ml cold ethylacetate with octylpyrocatechin inhibitor was added. Approximately 0.505 ml of a 1:1 dilution of HCl in water were slowly dropped into the ethylacetate mixture until a pH of 2-3 was obtained. The ethylacetate layer was removed and the water layer was extracted 3 times (4 ml each) with ethylacetate. The ethylacetate fractions were combined and extracted 3 times with water (5 ml) to remove unreacted Leu-Gly and dried with sodium sulfate. The solution was filtered and evaporated to dryness. Dry ether with octylpyrocatechin inhibitor was added to the dry mixture and it was refrigerated overnight and then filtered. Crystals were washed with ether and desiccated. The yield of pure product was 320 mg with a melting point $150°-154°$ C. TLC analysis (10:2:0.5 acetone:ether:acetic acid) indicated the disappearance of reactants in the reaction mixture.

Methacryloylglycylphenylalanylleucylglycyl p-Nitrophenyl Ester (MA-Gly-Phe-Leu-Gly-ONp) Preparation:

MA-Gly-Phe-Leu-Gly from different reactions was combined for the synthesis of MA-Gly-Phe-Leu-Gly-ONp according to the following reaction sequence:

Synthesis of MA—G—F—L—G—ONp

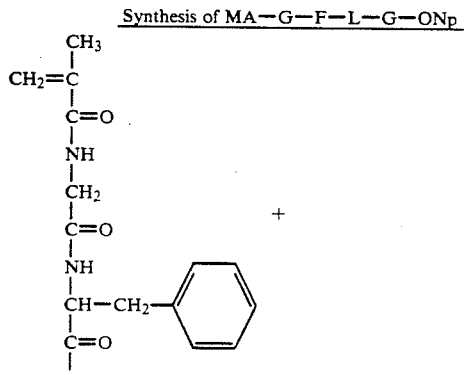

+

-continued
Synthesis of MA—G—F—L—G—ONp

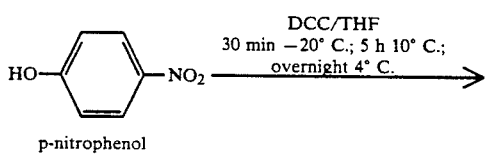

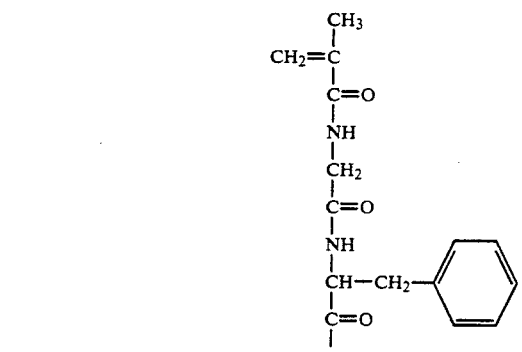
p-nitrophenol

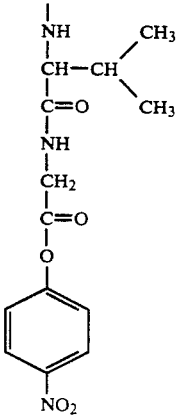

MA-Gly-Phe-Leu-Gly (0.5 g, $1.09 \times 10^{-3}$ moles) and 0.166 g ($1.19 \times 10^{-3}$ moles) p-nitrophenol were dissolved in 8.1 ml dry THF under warm tap water. The mixture was cooled to −20° C. DCC (0.269 g, 1.3×10⁻³ mole) dissolved in approximately 1.1 ml THF was slowly dropped into the mixture. The reaction proceeded for 0.5 hours at −20° C., 5 hours at −10° C., and overnight at 4° C. Octylpyrocatechin inhibitor was added and the mixture was stirred for 24 hours more at room temperature. Acetic acid (12.5 μl) was dropped into the mixture and stirring continued for 30 min. DCU was filtered off. The product was dissolved in ethylacetate and refrigerated for 1 hour. The DCU was filtered off and the ethylacetate was evaporated. The product was dissolved in ethylacetate, filtered and rotoevaporated to dryness two additional times. This product was soaked in ether overnight, filtered, and dried. This substance was crystallized from acetone: ether 3:1. The main yield was 287 mg with a melting point 122°–126° C. The extinction coefficient was $\epsilon_{269} = 10^4$ l/mole.cm (DMSO) determined spectrophotometrically. Amino acid analysis confirmed the structure; the ratio of Gly:Phe:Leu was determined as 2:1:1.

The synthesis of the copolymer precursors, using monomers from Examples 1–4, which were utilized to prepare Copolymers I through V is given in Examples 5 and 6 which follow.

Example 5

Polymer-Gly-ONp Preparation

A copolymer of HPMA (Example 1) and MA-Gly-ONp (Example 2), identified as either Precursor 1a or 1b, was prepared according to the reaction sequence:

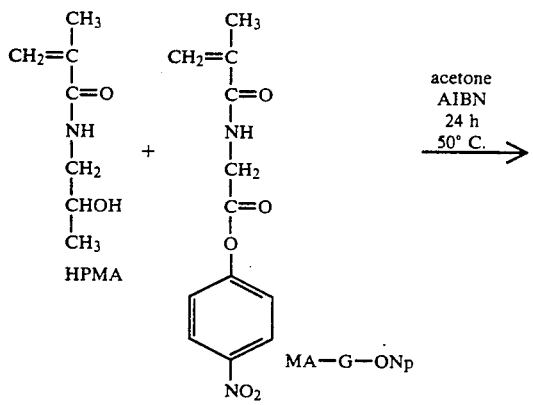

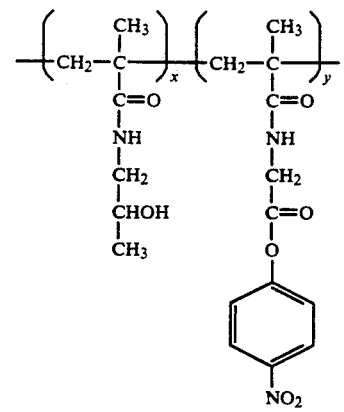

Polymer-Gly-ONp (Precursor 1a) was prepared by radical precipitation copolymerization in acetone of HPMA (2.26 g, 85 mole %) and MA-Gly-ONp (0.74 g, 15 mole %) using 0.144 g azoisobutrynitrile (AIBN) with weight percentages of 12.5% monomers, 86.9% acetone, and 0.6% AIBN. The monomers plus AIBN were dissolved in the acetone, filtered, transferred to an ampule, and bubbled with N₂. The ampule was sealed and the mixture polymerized at 50° C. for 48 hours. The polymer was filtered, washed with acetone and dry ether, and desiccated. The polymer was dissolved in MeOH and reprecipitated into acetone, washed with acetone and ether and desiccated. The yield of purified product was 1.52 g. The content of ONp determined by spectroscopy ($\epsilon_{274} = 0.95 \times 10^4$ l/mole.cm DMSO) was 10.6 mole %. The weight averaged molecular weight (17,000) and polydispersity (1.5) were determined after aminolysis with 1-amino-2-propanol by FPLC analysis on a Superose 12 column (10×30 cm) calibrated with fractions of polyHPMA (buffer 0.5M NaCl+0.05M TRIS; pH 8).

Precursor 1b was similarly synthesized and contained 5.1 mole % ONp with a weight averaged molecular weight of 23,000 and polydispersity of 1.5.

Example 6

Polymer-Gly-Phe-Leu-Gly-ONp Preparation

A copolymer of HPMA (Example 1) and MA-Gly-Phe-Leu-Gly-ONp (Example 4), identified as either Precursor 2a or 2b, was prepared according to the reaction sequence:

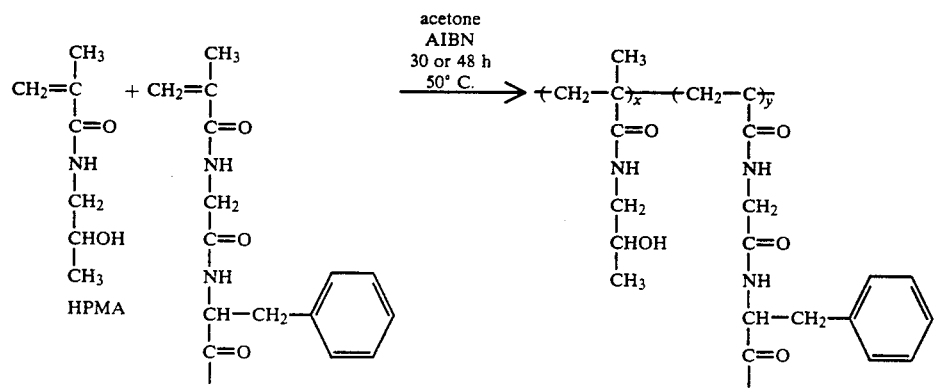

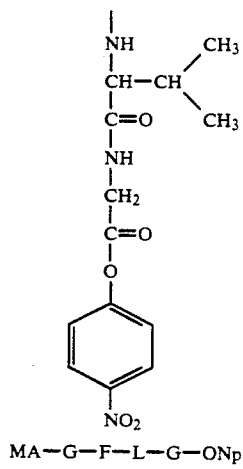

MA—G—F—L—G—ONp

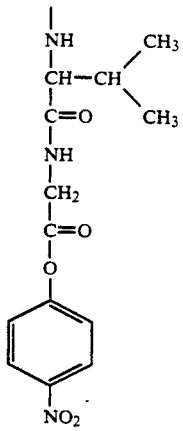

Copolymers containing two different quantities of Gly-Phe-Leu-Gly-ONp side chains were synthesized. The one with the lower amount (identified Precursor 2a) was used in the synthesis of the individual copolymers [Polymer-Gly-Phe-Leu-Gly-ce$_6$ (Copolymer III) and Polymer-Gly-Phe-Leu-Gly-adria (Copolymer 1)] and the one with the higher amount (Precursor 2b) was used in the synthesis of the combination copolymer

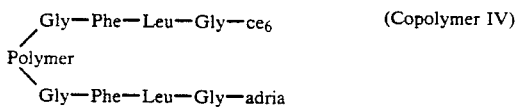   (Copolymer IV)

For Precursor 2a, 726 97 mg (96 mole %) HPMA, 123.02 mg (4 mole %) MA-Gly-Phe-Leu-Gly-ONp and 41 mg AIBN were dissolved in 7.5 ml acetone. The solution was filtered, transferred to an ampule and bubbled with $N_2$. The ampule was sealed and the monomers copolymerized at 50° C. for 30 hours. The precipitated copolymer was filtered, washed with acetone and ether, and desiccated. It was then dissolved in MeOH (18 wt %) and reprecipitated into 100 ml acetone:ether 3:1. The final yield was 570.5 mg of copolymer with 3.7 mole % ONp ($\epsilon_{274}=0.95\times10^4$ 1/mole.cm in DMSO) determined by UV spectroscopy. The weight average molecular weight (21,000) and polydispersity (1.6) were determined after aminolysis with 1-amino-2-propanol by FPLC analysis on a Superose 12 column (10×30 cm) calibrated with fractions of polyHPMA (buffer 0.5M NaCl+0.05M TRIS; pH 8).

Precursor 2b was prepared by radical precipitation copolymerization in the same manner. HPMA (206.7 mg, 90 mole %), MA-Gly-Phe-Leu-Gly-ONp (93.3 mg, 10 mole %), and AIBN (14.4 mg) were dissolved in 2.65 ml acetone. Copolymerization proceeded for 48 hours at 50° C. The final yield of copolymer was 197.5 mg with 7.8 mole % ONp ($\epsilon_{272}=0.95\times10^4$ mole.cm in DMSO) determined spectrophotometrically. The weight average molecular weight (18,000) and polydispersity (1.6) were determined after aminolysis with 1-amino-2-propanol by FPLC analysis on a Superose 12 column (10×30 cm) calibrated with fractions of polyHPMA (buffer 0.5M NaCl+0.05M TRIS; pH 8) The 7.5 mole % of cleavable side chains in Precursor 2b was about the upper limit which could be present and the polymer still retain solubility in physiological solutions, particularly when attaching of hydrophobic drugs to the polymer to the side chain.

The synthesis of the Copolymers I through VI using precursor copolymers from Examples 5 and 6 is given in Examples 7-12 which follow.

The anticancer drug when utilized in the examples which follow, is adriamycin hydrochloride (adria) which has the structure:

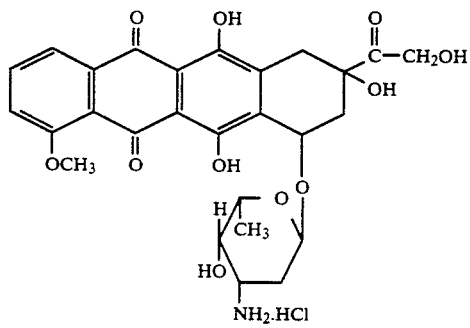

The photoactivatable drug, when utilized in the examples which follow, is meso-chlorin e$_6$ monoethylene diamine disodium salt (ce$_6$) which has the structure:

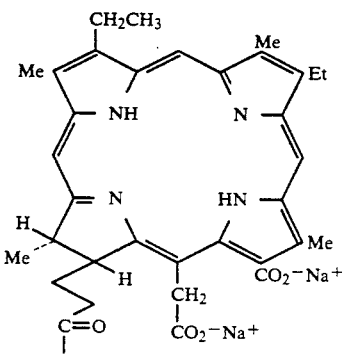

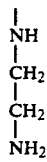

Example 7

Polymer-Gly-ce$_6$ (Copolymer III) Preparation

Copolymer III, containing nondegradable side chains, was prepared containing ce$_6$ at a wt % of 11.2 (Copolymer IIIa), 7.9 (Copolymer IIIb) and 8.3 (Copolymer IIIc) respectively according to the reaction sequence:

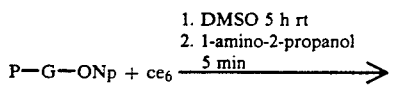

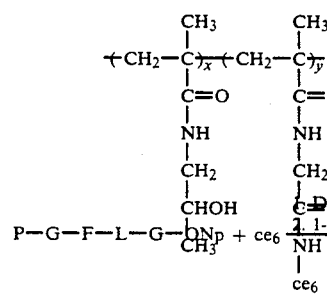

Copolymer IIIa was synthesized as follows: Polymer-Gly-ONp (Precursor 1a having a molecular weight of about 17,000 and a polydispersity of 1.5) (225 mg, 10.6 mole % ONp) was dissolved in 0.8 ml DMSO. Mesochlorin e$_6$ monoethylenediamine disodium salt (ce$_6$) (39.4 mg, 57.5 μmole) (Porphyrin Products, Logan, Utah) was dissolved in 0.4 ml DMSO. The ce$_6$ solution were added to the P-ONp solution (0.3 ml more DMSO was added for washing) and stirred for 5 hours at room temperature. Next, 25.7 μl 1-amino-2-propanol was added and the mixture was stirred 15 minutes at room temperature. The solution was precipitated into acetone and refrigerated overnight. The polymer was filtered, washed with acetone and ether and then desiccated. It was dissolved in MeOH (3.5 ml) and applied to an LH-20 column (55×3 cm). The main polymer fraction was collected, rotoevaporated to dryness, dissolved in distilled water, frozen, and lyophilized. The main peak contained 142.3 mg and the total polymer collected was 217 mg. The chlorin content determined spectrophotometrically ($\epsilon_{394} = 1.58 \times 10^5$ l/mole.cm in methanol) was 11.2 wt % (2.6 mole %).

Copolymers IIIb and IIIc were similarly synthesized from precursor copolymers 1b (molecular weight of about 23,000 and polydispersity of 1.5) and 1a (molecular weight of about 17,000 and polydispersity of 1.5), respectively and contained 7.9 and 8.3 wt % ce$_6$, respectively.

Example 8

Polymer-Gly-Phe-Leu-Gly-ce$_6$ (Copolymer II) Preparation

Copolymer II, containing degradable side chains, was prepared with a ce$_6$ content of 11.2 wt % according to the reaction sequence:

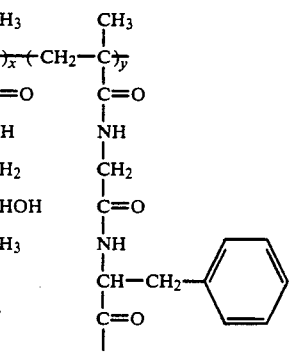

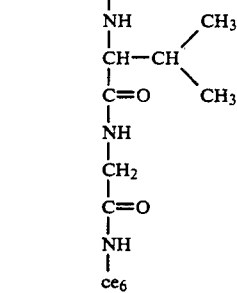

Polymer-Gly-Phe-Leu-Gly-ONp (Precursor 2a having a molecular weight of about 21,000 and a polydispersity of 1.6) (200 mg, 3.7 mole % ONp) was dissolved in 0.75 ml DMSO. Ce$_6$ (32.9 mg) in a 1.25 times molar excess was dissolved in 0.15 ml DMSO. The ce$_6$ mixture was added to the polymer mixture (an additional 0.2 ml DMSO added for washing) and stirred for 4 hours at room temperature. One-amino-2-propanol (6.4 μl) in 3 times excess of the theoretical remaining ONp groups was added and the mixture was stirred for 5 additional minutes. The copolymer was precipitated into a 3:1 acetone:ether mixture, filtered, washed with acetone and ether, and desiccated. The copolymer was then dissolved in 5 ml MeOH and applied to an LH-20 column (55×3 cm). The copolymer band was collected, evaporated to dryness, dissolved in distilled water, frozen, and lyophilized. The yield of pure product was 168 mg with 11.2 wt % $ce_6$ determined spectrophotometrically ($\epsilon_{394}=1.58\times10^5$ l/mole.cm in methanol).

Example 9

Polymer-Gly-Phe-Leu-Gly-adria (Copolymer I) Preparation

Copolymer I, containing degradable sidechains, was prepared with adriamycin content of 7.4 wt % according to the reaction sequence:

Polymer-Gly-Phe-Leu-Gly-ONp (Precursor 2a having a molecular weight of about 21,000 and a polydispersity of 1.6) (200 mg, 3.7 mole % ONp) was dissolved in 0.76 ml DMSO. Adriamycin.HCl (27.8 mg, $4.8\times10^{-5}$ mole) was dissolved in 0.18 ml DMSO and added to the dissolved polymer. Triethylamine (5.35 μl, $3.84\times10^{-5}$ mole) was added. The reaction mixture was stirred for 1 hour at room temperature at which time twenty percent more triethylamine (2.7 ml, $9.6\times10^{-6}$ mole) was added. The reaction progressed for 3 hours at room temperature. One-amino-2-propanol (6.4 μl) in 3 times excess of theoretical remaining ONp groups was added and the mixture was stirred 5 minutes more. The product was precipitated into 4.75 ml acetone:ether 4:1 and refrigerated for 1 hour. It was then filtered, washed with acetone and ether, and desiccated. The product was dissolved in 5 ml MeOH and applied to an LH-20 column (55×3 cm). The main polymer peak was collected, evaporated to dryness, frozen, and lyophilized. The adriamycin content ($\epsilon_{488}=1.19\times10^4$ l/mole.cm in water) was approximately 9.0 wt % and the final yield was 183 mg.

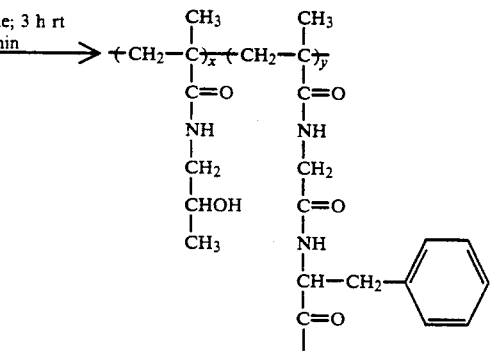
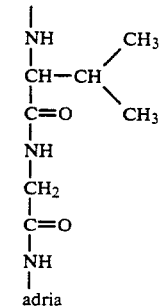

Example 10

Polymer(Gly-Phe-Leu-Gly-adria)Gly-Phe-Leu-Gly-$ce_6$ (Copolymer IV) Preparation

Combination Copolymer IV, containing degradable side chains, was prepared with $ce_6$ content 4.2 wt % and adriamycin content 7.25 wt % according to the reaction sequence:

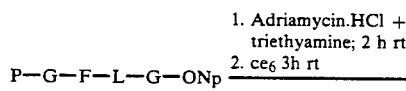
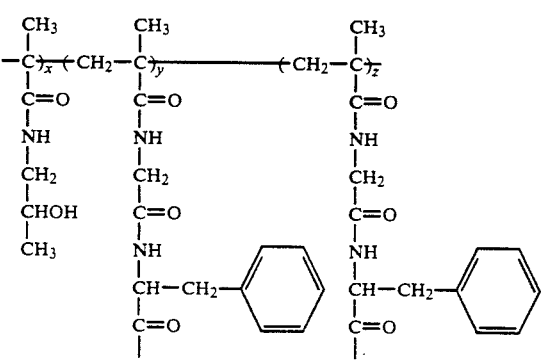

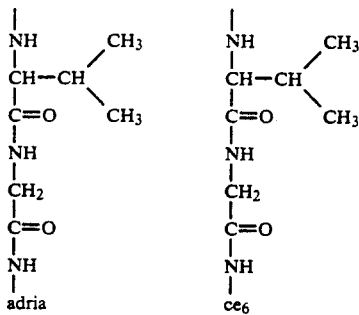

Forty mg Polymer-Gly-Phe-Leu-Gly-ONp (Precursor 2b having a molecular weight of about 18,000 and a polydispersity of 1.6) (7.8 mole % ONp) were dissolved in 0.10 ml DMSO. Adriamycin-HCl (4.6 mg, 7.9 μmole) dissolved in 0.12 ml DMSO was added to the polymer solution. Triethylamine (0.88 μl, 6.3 μmole) was added. The reaction proceeded for 1 hour at room temperature. Forty percent (0.44 μl, 3.2 μmole) more triethylamine was added and the reaction proceeded for 1 hour more. A portion (0.06 ml) of the solution was removed for analysis of adriamycin. The content of adriamycin was estimated to be 7.25 wt % by spectroscopy ($\epsilon_{450} = 1.19 \times 10^4$ in water). To the solution, 1.75 mg (2.6 μmole) ce$_6$ dissolved in 0.03 ml DMSO were added. Triethylamine (0.44 μl) was added. The reaction mixture was stirred 3 hours. One-amino-2-propanol (2.1 μl, 27 μmole) was added and the mixture was stirred for 5 minutes more. The solution was precipitated into acetone:ether 3:1 (400 ml) and refrigerated 3 hours. The polymer was filtered, washed with acetone and ether, and desiccated. The polymer was dissolved in approximately 5 ml MeOH and applied to an LH-20 column (55×3 cm) equilibrated with MeOH. The yield of purified product was 27.1 mg containing approximately 4.2 wt % ce$_6$ determined by spectroscopy ($\epsilon_{394} = 1.58 \times 10^5$ l/mole.cm in MeOH).

Example 11

Polymer (Gly-Secretin)Gly-ce$_6$ (Copolymer V) Preparation

Copolymer V, containing nondegradable sidechains, was prepared according to the reaction sequence:

$$P-G-ONp + ce_6 + \text{aecretin} \xrightarrow[\text{2. triethylamine}]{\text{1. DMSO}} \xrightarrow{30 \text{ h rt}}$$

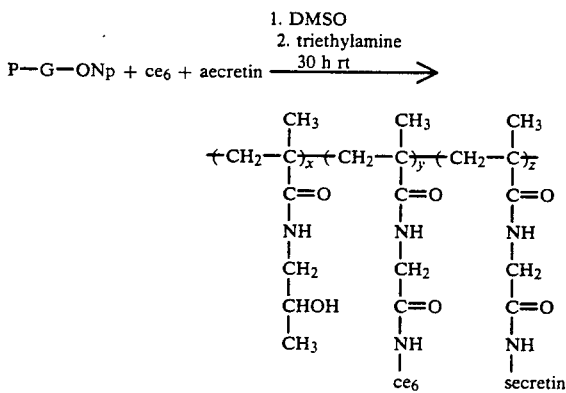

Fifteen mg of Polymer-Gly-ONp (Precursor 1a having a molecular weight of about 17,000 and a polydispersity of about 1.5) were dissolved in 50 μl DMSO. Two mg of ce$_6$ (2.9 μmole) were dissolved in 30 μl DMSO and added to the polymer solution. Next, 19 mg (6.2 μmole) secretin (porcine) dissolved in 110 μl DMSO were added to the mixture. Ten μl (7.5 μmole) of triethylamine (10 times dilution in DMSO) were added to the reaction mixture. After 1 hour stirring at room temperature, 5 μl (3.7 μlmole) more triethylamine were added. Five μl (3.7 μmole) more triethylamine were added 1 hour later. The mixture was stirred for 30 hour at room temperature. The reaction mixture was diluted with 2.5 ml of water and dialyzed in 20% ethanol in water for 8 hours, 4° C. (6000–8000 MWCO) to remove the organic solvent. Next it was dialyzed for 40 hours more in water. Then it was dialyzed 24 hours in water [12,000–14,000 molecular weight cut off (MWCO)] to be sure all unreacted secretin was removed (the absence of free secretin was verified on an FPLC column (HR 10/30 column; Superose 12; 0.05M TRIS+0.5M NaCl, pH 8). The free drug was separated out on a PD-10 column equilibrated with water. The sample was frozen and lyophilized. The content of ce$_6$ was determined by UV spectroscopy ($\epsilon_{400} = 10^5$ in DMSO) to be 5.9 wt % ce$_6$ and the content of secretin was determined to be 300 μg/mg conjugate by amino acid analysis after hydrolysis with 6N HCl.

Example 12

Polymer(Gly-Phe-Leu-Gly-adria)(Gly-Phe-Leu-Gly-ce$_6$)Gly-Phe-Leu-Gly-Secretin)(Copolymer VI) Preparation Four hundred mg of P-Gly-Phe-Leu-Gly-ONp (Precursor 2b; 7.8 mole % ONp: $M_w = 18,000$; polydispersity 1.6) is dissolved in 1 ml of dimethylsulfoxide (DMSO). Adriamycin.HCl (23 mg; 40 μmole) dissolved in 0.6 ml DMSO is added to the copolymer solution, followed by the addition of 4.4 μl (32 μmole) of triethyamine. After 1 h at room temperature 2.2 μl (16 μmole) of triethyamine is added followed after 1 h by the addition of the solution of 8.75 mg (12 μmole) of ce$_6$ dissolved in 0.15 ml of DMSO. The reaction mixture is stirred for 3 h. Four hundred mg of secretin (13 mmole) is added and the reaction continued overnight at room temperature. The reaction mixture is dialyzed against 10% ethanol in water for 5 h and against pure water for 48 h, frozen and lyophilized.

Other copolymers may be used to prepare combination polymers having an anticancer agent and a photoactivatable drug attached to the polymer chain. The following examples are illustrative of how such polymers can be prepared.

Example 13

One gram of dextran (MW 40,000) and 35 mg of 4-(N,N,-dimethylamino)pyridine were dissolved in 20 ml of dimethylsulfoxide/pyridine (v/v=1:1). To this solution was added 500 mg of p-nitrophenyl chloroformate in three portions. After 20 minutes the reaction mixture was precipitated into an excess of absolute ethanol, washed and dried in vacuo. The content of p-nitrophenyl groups, as determined by UV spectrophotometry was 5.1 mole %.

Example 14

A solution is prepared by dissolving 500 mg of activated dextran (prepared according to Example 13 and containing about $1.5 \times 10^{-4}$ mol of active groups) in 8 ml of dimethylsulfoxide. A solution of $1 \times 10^{-4}$ mol of adriamycin hydrochloride and $1 \times 10^{-4}$ mol of N-(2-aminoethyl)chlorin $e_6$-amide in 2 ml of dimethylsulfoxide is added, followed by the addition of $1 \times 10^{-4}$ mol of triethylamine. After 5 hours of reaction, $2 \times 10^{-4}$ mol of 1-amino-2-propanol is added. Ten minutes later the polymer, containing both adriamycin and $ec_6$ moieties, is isolated by precipitation, sucked off, washed and dried in vacuo.

Example 15

Poly(1-vinyl-2-pyrrolidone-co-maleic anhydride, (MW 20,000) is prepared according to the method of J. Pato et al., Makromol. Chem. Rapid Commun., 3, 643 (1982). A solution is prepared by dissolving 200 mg of this copolymer in dry dimethylformamide. A solution containing $1 \times 10^{-4}$ mol of puromycin and $1 \times 10^{-4}$ mol of N-(2-aminoethyl) mesochlorin $e_6$-amide dissolved in 1 ml of dimethylformamide is added to the copolymer solution and reacted for 3 h at 40° C. The product of the reaction is isolated by precipitation into diethyl ether and dried in vacuo. The polymer-drug conjugate is dissolved in hot water to hydrolyse the unreacted anhydride groups. The solution is then cooled, dialyzed for 72 hours in a Visking dialysis tubing against water and freeze dried.

In Vitro Studies

Example 16

Photophysical Analyses

Both direct and indirect methods for excited state determination were performed in the comparison of photophysical properties of free $ce_6$ and the noncleavable Polymer-Gly-$ce_6$ (Copolymer IIIb). Time resolved fluorescence measurements were performed at the Center for Fast Kinetics Research (CFKR), University of Texas at Austin using a single photon counting technique (Atherton et al., J. Phys. Chem., 93, 6809(1989). An on-line, computerized flash kinetic spectrophotometer was used to determine triplet-singlet difference spectra, and triplet lifetimes. Excitation was carried out with a Quantel YG 481 Q-switched Nd:YAG laser. The quantum yield of singlet oxygen generation ($\Phi^1\Delta\hat{g}$) was determined subsequent to a 355 nm pulsed laser excitation of the photosensitizers in air saturated D$_2$O by following the emission of singlet oxygen (1270 nm) over time.

For the indirect method, the quantum yield of oxygen uptake was calculated from measurements of a decrease in oxygen concentration with a recording oxygen electrode system as the ratio (initial rate of uptake of oxygen molecules)/(initial rate of absorption of photons). The reaction mixtures contained the photosensitizer and furfuryl alcohol as a substrate. Furfuryl alcohol was chosen because it reacts chemically with singlet oxygen with good efficiency (rate constant $1.2 \times 10^8$). In addition, it does not react with hydrogen peroxide or superoxide and most likely does not undergo radical initiated autooxidation (Maurette et al., Helv. Chim. Acta, 66, 722(1983) and Haag et al., Chemosphere, 13, 631(1984). Reaction mixtures were illuminated with a 500 W slide projector provided with a 407 nm interference filter (bandwidth $10\pm2$ nm at 50% peak transmittance) and a time dependent decrease in oxygen concentration was recorded. Incident light energy was measured with a vacuum thermocouple-millimicrovoltmeter calibrated with standard lamps. Incident light fluence rates were approximately 2 mW/cm$^2$. The fraction of light absorbed was determined with a silicon photodiode photometer. Quantum yields of singlet oxygen generation were estimated from the quantum yield of oxygen uptake values at saturating furfuryl alcohol concentrations using rose bengal as a standard. Errors in quantum yield measurements were $\pm5$-10%. This procedure was repeated using Polymer-Gly-Phe-Leu-Gly-$ce_6$ (Copolymer II) to compare the difference in quantum yield of oxygen generation with that of Polymer-Gly-$ce_6$ containing only glycine in its side chain.

Singlet Oxygen Generation

Direct evidence for $1\Delta\hat{g}$ singlet oxygen production was given by its emission at 1270 nm following flash excitation at 355 nm of 30 $\mu$mole $ce_6$ or Polymer-Gly-$ce_6$ in sodium phosphate buffer (pH 7.4) in D$_2$O. The near IR emission decayed by a first order process with lifetimes of $54.4\pm1$ and $50.1\pm1.5$ $\mu$s for $ce_6$ and for Polymer-Gly-$ce_6$, respectively. These values are in the range of the reported value of 55 $\mu$s for singlet oxygen decay in D$_2$O. The quantum yields of oxygen uptake during the $ce_6$, Polymer-Gly-$ce_6$ (copolymer IIIb), and rose bengal sensitized photooxidation of furfuryl alcohol vs. furfuryl alcohol concentration reach a maximum and begin to level off at approximately 50 mM furfuryl alcohol. All of the singlet oxygen produced are being quenched by furfuryl alcohol in this range. The ratio of the quantum yields of oxygen uptake in this range (saturating concentrations of furfuryl alcohol) and the literature value of quantum yield of singlet oxygen generation for rose bengal (0.75) makes possible the calculation of quantum yield of singlet oxygen generation $\phi^1\Delta\hat{g}$ of Polymer-Gly-$ce_6$ and free $ce_6$. (see Table 1 for results)

TABLE 1

| Quantum Yields of Singlet Oxygen Generation ($\phi^1\hat{g}$) of Free $ce_6$ and Polymer-Gly-$ce_6$. | | |
|---|---|---|
| Sample | Solution | $\phi^1 g$ |
| $ce_6$ | buffer pH 7.4 | 0.73 |
| $ce_6$ | buffer + CTAB | 0.81 |
| Polymer*-Gly-$ce_6$ | buffer pH 7.4 | 0.25 |
| Polymer*-Gly-$ce_6$ | buffer + CTAB | 0.83 |

*Copolymer IIIb: CTAB: Cetyltrimethylammonium bromide; Buffer: 100 mM sodium phosphate buffer (pH 7.4)

For the Polymer-Gly-Phe-Leu-Gly-$ce_6$ (Copolymer II) in PBS at a 100 mM concentration of furfuryl alcohol, the quantum yield of oxygen uptake was found to be 0.06, slightly lower than that of Polymer-Gly-$ce_6$ (Copolymer IIIb) (quantum yield of oxygen uptake 0.1). However, when CTAB was added, the value increased to 0.39, comparable to values for the $ce_6$ and Polymer-Gly-$ce_6$ measured with added CTAB.

These data show that it is not necessary for the $ce_6$ to be cleaved from the copolymer to have photodynamic effect. However, the solution properties of copolymer bound $ce_6$ greatly affects its quantum yield of singlet oxygen generation. The Polymer-Gly-ce$_6$ had a much lower yield of singlet oxygen generation in sodium phosphate buffer than did the free drug. Adding detergent (CTAB) to both enhanced the quantum yield of the free ce$_6$ by a small amount and substantially enhanced the quantum yield of singlet oxygen of the Polymer-Gly-ce$_6$. This indicates that Polymer-Gly-ce$_6$ is much more aggregated in buffer than the free drug, although some monomerization takes place for the free drug when the surfactant is added. Evidence of aggregation is seen by shorter, broader peaks in the absorbance spectrum and quenching of the fluorescence spectrum of the Polymer-Gly-ce$_6$ in buffer compared with ce$_6$. Micellar aggregates are formed in aqueous solution as the hydrophobic ce$_6$ molecules are repelled by the water forming a hydrophobic core with the hydrophilic polymer forming the outer shell in contact with the water.

Triplet State Properties

Usually, oxygen requiring photosensitized reactions in biological systems are possible because of long-lived triplet states of the photosensitizer. A triplet-singlet difference spectrum was recorded by measuring absorbance of either ce$_6$ or Polymer-Gly-ce$_6$ solutions in sodium phosphate buffer (pH 7.4) 1.2 μs following a 355 nm flash in air. The most useful triplet absorption peak was found to be at 430 nm for both sensitizers. Triplet lifetimes of the sensitizers were measured at this wavelength under argon. They were found to be 400 μs for ce$_6$ and 450 μs for Polymer-Gly-ce$_6$.

Photobleaching

The quantum yields of photobleaching for ce$_6$ and Polymer-Gly-ce$_6$ (Copolymer IIIb) were measured as the (initial rate of disappearance of sensitizer molecules)/(initial rate of absorption of photons). The disappearance of molecules was monitored spectrophotometrically at various time intervals of illumination with the same 500 mW incandescent lamp with a 407 nm bandpass filter as used in photooxidation experiments. Error in these measurements was also 5–10%.

TABLE 2

Quantum Yields of Photobleaching of Free ce$_6$ and Polymer-Gly-ce$_6$.

| Solution | ce$_6$ | Polymer-Gly-ce$_6$ |
|---|---|---|
| buffer (pH 7.4) | $1.3 \times 10^{-3}$ | $2.8 \times 10^{-4}$ |
| buffer + 10 mM furfuryl alcohol | $1.2 \times 10^{-3}$ | $2.5 \times 10^{-4}$ |
| buffer + 0.5% HSA | $6.8 \times 10^{-4}$ | $4.8 \times 10^{-4}$ |
| buffer + CTAB | $4.9 \times 10^{-4}$ | $5.9 \times 10^{-5}$ |

Polymer-Gly-ce$_6$: Copolymer IIIb; HSA: Human serum albumin; Buffer: 100 mM sodium phosphate (pH 7.4).

Table 2 lists the quantum yields of photobleaching of ce$_6$ and Polymer-Gly-ce$_6$ (Copolymer IIIb) under different reaction conditions. The reaction mixtures were 5 μM of sensitizer in air saturated (0.22 mM oxygen) and 100 mM sodium phosphate buffer (pH 7.4). Ce$_6$ photobleaching followed first order kinetics until 60% of the sensitizer had been bleached. No new peaks were observed in the visible spectrum during photobleaching indicating that the macrocycle was being destroyed. Furfuryl alcohol had little effect while HSA decreased the quantum yield to approximately 50% of the control. CTAB, however, inhibited photobleaching of Ce$_6$.

On the other hand, photobleaching of Polymer-Gly-ce$_6$ did not follow first order kinetics and the quantum yield was only 20% of that of the ce$_6$. Similarly, no new peaks in the visible spectrum were apparent. The main differences in the results with Polymer-Gly-ce$_6$ compared with ce$_6$ were that HSA somewhat increased the quantum yield for Polymer-Gly-ce$_6$ and the detergent (CTAB) only slightly inhibited photobleaching.

Photobleaching may be useful in PDT such that light can penetrate deeper and deeper into tumor tissue as the compound photofades after its PDT effect has been exerted. The sensitizer deeper in the tumor can then be activated. If there is a large quantity of sensitizer in the upper layer, it will absorb the light and prevent it from penetrating the tumor.

Example 17

Cleavage of ce$_6$ from Polymer-Gly-Phe-Leu-Gly-ce$_6$ with Cathepsin B

Preliminary experiments were performed to characterize the activity of Cathepsin B, a lysosomal cysteine protease isolated from bovine spleen. The molar extinction coefficient, $\epsilon_{281} = 5.15 \times 10^4$ l/mole.cm (0.09M phosphate buffer, pH 6) was determined spectrophotometrically (MW=28,000 (Pohl et al. FEBS Lett., 23, 142(1982)). Various concentrations of enzyme were examined to find one with sufficient activity. A reaction mixture concentration of 0.53 mg Cathepsin B (19 μmole) plus 1.54 mg (5 μmole) glutathione plus 1.0 mg (0.025 ml of 40 mg/ml in DMF) (2.3 mmole) N$^\alpha$-benzoyl-L-arginine-p-nitroanilide (BAPNA) for the substrate was used. The phosphate buffer (0.09M, pH 6) was initially bubbled with N$_2$. Solutions were then prepared and kept on ice. The enzyme, glutathione, and buffer mixture was bubbled with N$_2$ for 5 minutes. The solution was then preincubated at 37° C. for 5 minutes for the glutathione to activate the enzyme binding site. The substrate (BAPNA) was rapidly added and the absorbance at 410 nm was monitored over time. This concentration gave an enzyme activity $\Delta A_{410}$/10 minutes = 1.76. To check activity over time mimicking the reaction conditions that would later be used with the polymer, the enzyme and glutathione in buffer were incubated for 120 hours (37° C.) at which time the substrate was added and the absorbance at 410 nm was monitored. The enzyme was still 68% active.

To determine the cleavage properties of Polymer-Gly-Phe-Leu-Gly-ce$_6$ (Copolymer II), first different enzyme and polymer concentrations were compared and the best combination was chosen. Stock solutions of polymer (1.9 mg/ml phosphate buffer), enzyme (2.12 mg/ml phosphate buffer), and glutathione (15.36 mg/ml) were prepared. Again, the buffer was initially bubbled with N$_2$. The stock enzyme (0.25 ml) plus 0.4 ml more buffer were bubbled with N$_2$ on ice for 5 minutes. Glutathione (0.1 ml) was added and the solution was preincubated for 5 minutes at 37° C. Stock polymer (0.25 ml) was added and the sample was flushed with N$_2$ and sealed. Five samples were prepared this way and incubated at 37° C. in the dark for 4, 8, 12, 24, and 49 hours. The reaction mixture at each time (0.95 ml plus 1.55 ml water was applied to a PD-10 column equilibrated with water, and 1 ml fractions were collected. (The columns were previously calibrated with both Polymer-Gly-Phe-Leu-Gly-ce$_6$ and free ce$_6$). The Polymer-Gly-Phe-Leu-Gly-ce$_6$ eluted in fractions 1–3 and the free drug in fractions 7–10. One milliliter of 1N NaOH was added after fraction 10 to release the free ce$_6$ nonspecifically bound to the column. One half milliliter of each fraction was placed into a cuvette and 50 μl of 10% Triton X-100 was added. The absorbance at 398 nm was recorded and the percent of cleaved ce$_6$ was calculated for each sample. (A control, Polymer-Glyce₆ copolymer was studied under the same conditions which did not show any cleavage ability).

The results of the cleavage experiments shows that ce₆ is cleaved from Polymer-Gly-Phe-Leu-Gly-ce₆. At 120 hours 87.5 percent cleavage was attained. The absorbance for fractions 7-10 (corresponding with the free ce₆) increases with a concomitant decrease in the absorbance of fractions 1-4 (corresponding with the amount of the decrease in Polymer-Gly-Phe-Leu-Gly-ce₆) over time. The exact values of the decrease in concentration of Polymer-Gly-Phe-Leu-Gly-ce₆ and the increase in free ce₆ were calculated and correlated. The recovery of material was calculated for each sample and was within a few percent of 100% for all samples.

Quantum Yield of Oxygen Uptake of Polymer-Gly-Phe-Leu-Gly-ce₆ After Cleavage with Cathepsin B The results of photophysical analyses comparing polymer bound ce₆ with free ce₆ as well as in vivo results comparing the cleavable (Copolymer II) and noncleavable (Copolymer IIIb) copolymers led to a study comparing the photophysical activity for the cleavable copolymer (Copolymer II) before and after enzymatic release of ce₆ by Cathepsin B. For this experiment, three samples were prepared. The stock solution concentrations and reaction mixtures were prepared in the same manner as in the previously described cleavage experiments. For two samples, stock solutions were mixed and the reactions proceeded at 37° C. in the dark for two days and for one week. The remaining sample was used as a control. It was incubated in parts; the enzyme and substrate were incubated separately for two days. They were mixed immediately before photophysical analysis. Oxygen uptake measurements were made using the furfuryl alcohol photooxidation method described in Example 16. Two hundred fifty microliters of the sample were diluted with 3.75 ml of phosphate buffer (pH 6) and the furfuryl alcohol saturating concentration of 100 mM was added. The solution was air saturated and equipped with an oxygen electrode. The decrease in oxygen concentration was measured as a function of time upon illumination of the sample with light (407 nm). The quantum yield of oxygen uptake of the sample was calculated from which the quantum yield of singlet oxygen was determined using previously determined values of rose bengal as a standard: 0.375 (quantum yield of oxygen uptake) and 0.75 (quantum yield of singlet oxygen generation), as a standard.

TABLE 3

Photophysical Properties After Cleavage
Photophysical Properties Affected by Enzymatic Cleavage
of ce₆ from Polymer-Gly—Phe—Leu—Gly-ce₆ with Cathepsin B.

| Incubation | $\phi^1{}_g$ |
|---|---|
| none | 0.14 |
| 2 day | 0.66 |
| 1 Week | 0.71 |

In accordance with the results of the other photophysical studies yielding higher quantum yields of singlet oxygen generation for free ce₆ compared with Polymer-Gly-ce₆ (Table 1) and evidence of ce₆ cleavage in the in vitro cleavage studies, the solution in which the polymer (Copolymer II) was incubated with Cathepsin B for 48 hours showed a five-fold higher quantum yield of singlet oxygen generation than the solution in which the enzyme and polymer were mixed an instant before measurements were taken (Table 3). After a one week incubation, the quantum yield is approaching the value of that of free ce₆. The quantum yields of oxygen uptake are also listed.

This study, in which the quantum yield of oxygen uptake was measured for the Polymer-Gly-Phe-Leu-Gly-ce₆ reaction mixture after both 48 hours and 1 week incubation periods with Cathepsin B, showed a marked increase in quantum yield with time of cleavage. As the ce₆ was cleaved from the polymeric carrier, the photophysical behavior became more and more like the free drug in solution. This may explain the increased antitumor effect of PDT which was found with the cleavable vs. noncleavable copolymer in vivo. The copolymers may be aggregated as a function of low pH inside of the lysosome to a greater extent than the free drug and as the drug is cleaved it is in its less aggregated state. One the other hand, conformational changes rather than aggregation may be responsible for the different values of quantum yield of singlet oxygen generation for the free and copolymer bound drugs. However this difference may only be discerned with light scattering experiments. This may explain why PDT with the noncleavable Polymer-Gly-ce₆ seemed to have less effect on tumor suppression than expected compared to free ce₆ (results not shown) based on the enhanced localization retention behavior of the copolymer. Even though more polymer may have localized in the tumor, its PDT effect was not as pronounced as the free drug in the cellular environment. However, a comparison of PDT effect in vivo of the free drug vs. the Polymer-Gly-ce₆ is not very accurate because of the insolubility of the free ce₆ at the concentrations desirable for effective PDT. In addition, the differences in uptake properties which indicate different uptake times for a maximum concentration of the free vs. Polymer-Gly-ce₆ in the tumor makes necessary the use of different lag times before tumor irradiation.

In Vivo Studies

Neuroblastoma is responsible for 8% of cancers diagnosed in children under 15 years old. Most cases are in children under five years old and most have metastatic disease at the time of diagnosis (50° % of infants and 75% of older children). Prognosis depends on many factors including age of the patient, stage of the disease at diagnosis and for patients older than one year, lymph node involvement. Neuroblastoma arises from the sympathetic ganglia which are formed from sympathogonia which migrate from the neural crest early in embryonic development. Because of its place of origin, there are many possible locations for its appearance. Any location along the sympathetic nervous system is a potential site for neuroblastoma. The usual place of a primary tumor is in the abdomen either in an adrenal gland (40%) or in a paraspinal ganglion (40%). There are also thoracic (15%) and pelvic primaries (5%) Neuroblastoma often displays periorbital metastatis (DeVita et al., *Cancer Principles and Practice*, Vol. 2, 3rd., pp. 1624–1631(1987)). Even with recent advances in tumor therapy, neuroblastoma has a poor prognosis. It often metastasizes to bone marrow and is difficult to detect (Chadwick et al., in *Receptors in Tumor Biology*, pp. 169–188(1986)).

Neuroblastoma is treated with tumor resection if localized. A unique feature of neuroblastoma is its ability to spontaneously regress. Residual tumor in the tumor bed after resection rarely results in recurrence (DeVita et al., supra). In unresectable localized neuroblastoma, and regional neuroblastoma, mixtures of tumor resection and chemotherapy are used. Chemotherapy (often mixtures of drugs) is used for disseminated disease. Chemotherapeutic agents including cyclophosphamide, doxorubicin (adriamycin), cisplatin, teniposide, etoposide, vincristine and dacarbazine are used. Radiation therapy is also used.

The molecular genetics of neuroblastoma is better understood than for any other human cancer (DeVita et al., supra), yet little is known about its cell surface. Monoclonal antibodies have been raised to antigens on the surface of human neuroblastoma cells both for diagnostic and therapeutic purposes. $^{131}$I-coupled monoclonal antibodies were effective against disseminated disease, but patients with large tumors did not respond (DeVita et al., supra).

Roth et al., J. Neurochem., 42, 1145(1984) found that a clone of neuroblastoma cells derived from the mouse C1300 tumor (N18TG2) has a specific secretin receptor which is coupled to adenylate cyclase. Secretin is a 27 amino acid hormone found in the gastrointestinal system where it regulates pancreatic secretion and has the sequence.

His Ser Asp Gly Thr Phe Thr Ser Glu    (SEQ ID NO: 10)
  Leu Ser Arg Leu Arg Asp Ser Ala Arg
    Leu Glu Arg Leu Leu Gln Gly Leu Val

However, secretin's importance in nervous tissue is not well known, and the neuroblastoma cells were used in their study as a model to investigate the specificity of the peptide receptor associated with adenylate cyclase in neurons. But the size of secretin is appealing which may permit penetration into solid tumors compared with an antibody targeting moiety.

The Neuro 2A neuroblastoma cell line was used for demonstration purposes because it forms a solid, difficult to cure tumor in A/J mice. A/J mice (5-6 weeks old) were routinely injected with approximately $1.5 \times 10^6$ viable C1300 neuroblastoma tumor cells in the right costal margin. When tumors became palpable treatment was initiated. Treatment and control groups consisted of five mice per group. The drugs were normally dissolved in phosphate buffered saline (PBS) and injected intravenously (IV) into the tail vein of the mice. Drug doses expressed in mg/kg drug were calculated based on the weight percent of the drug bound to the copolymers. For the controls and treatment with the chemotherapeutic agent, tumor volumes were followed by measuring the length, width, and height of the tumors with calipers after drug administration.

For the photodynamic therapy treatments, an optimal time lag after drug administration was determined from localization/retention experiments after which light of 650 nm (argon dye laser) was applied. Several experiments were performed to determine suitable light and drug doses. The anticancer effect was similarly followed by measuring tumor volume. In the mixed experiments, the drugs were dissolved together and injected into the tail vein. A time lag was allowed for the adriamycin to take effect and for optimal photosensitizer uptake before light was applied.

All data for in vivo experiments are represented as the mean value of the number of mice in the group.

Example 18

Chemotherapy

Polymer-Gly-Phe-Leu-Gly-adria (7.4 wt % adriamycin.HCl) (Copolymer 1) was utilized to demonstrate tumor reduction effects. All experiments consisted of a control and Copolymer I at an adriamycin dosage of either 4.1 mg/kg, 8.2 mg/kg, or 16.4 mg/kg. The drugs were dissolved in bacteriostatic saline and injected IV into the tail vein. Tumor growth was followed by recording tumor volume. The treatment day was considered to be day zero and tumor volumes were followed until tumor burdens were indistinguishable from controls. Survivors were followed until day 55 after treatment.

The results, recorded in terms of tumor volume/time are given in Tables 4-6 for the various dosage ranges.

TABLE 4

| Time | Mean Tumor Vol. (mm$^3$) | |
|---|---|---|
| Days | 4.1 mg/kg | Control |
| 3 | 250 | 250 |
| 5 | 500 ± 200 | 500 ± 200 |
| 6 | 700 ± 250 | 1000 ± 250 |
| 9 | 1200 ± 200 | 2250 ± 350 |
| 13 | 2600 ± 400 | 5500 ± 1000 |

TABLE 5

| Time | Mean Tumor Vol. (mm$^3$) | |
|---|---|---|
| Days | 8.2 mg/kg | Control |
| 2 | 200 | 200 |
| 4 | 200 | 500 ± 200 |
| 6 | 200 | 950 ± 150 |
| 8 | 300 ± 200 | 1800 ± 200 |
| 10 | 550 ± 150 | 2800 ± 600 |
| 13 | 800 ± 300 | 4000 ± 800 |
| 15 | 1200 ± 500 | 5300 ± 1000 |
| 17 | 1300 ± 500 | 7000 ± 1200 |

TABLE 6

| Time | Mean Tumor Vol. (mm$^3$) | |
|---|---|---|
| Days | 16.4 mg/kg | Control |
| 0 | 100 | 100 |
| 3 | 200 | 250 |
| 5 | 50 | 600 |
| 6 | 0 | 1000 ± 100 |
| 9 | 0 | 2400 ± 400 |
| 13 | 0 | 5500 ± 1000 |

As shown in Table 6, the 16.4 mg/kg dose was 100% effective in curing tumors. All of the mice in this group remained tumor free and healthy followed until day fifty-five at which time they were sacrificed (this same dose of free drug was toxic to mice). The 4.1 mg/kg dose group behaved without substantial effect compared with the controls. The 8.2 mg/kg dose had some effect on tumor suppression, but no cure rate. Tumor growth was suppressed for approximately five days. By day ten, tumors were growing at the same rate as the controls. The 8.2 mg/kg concentration was used in subsequent mixed experiments.

Adriamycin (doxorubicin, NSC 123127) shows cumulative dose-dependent cardiomyopathy which is its principal dose-limiting side effect. This limits its long-term use in it free state. Toxicity is apparent with a single dose (16.4 mg/kg) of free adriamycin, whereas this dose of Polymer-Gly-Phe-Leu-Gly-adria reduces tumors. At an even higher dose (20 mg/kg) the free drug causes 100% morbidity. This dose causes initial weight loss in the mice in the first few days after administration of the Polymer-Gly-Phe-Leu-Gly-adria which is quickly regained.

Example 19

Localization/Retention Experiments

Localization/Retention experiments were performed to compare the uptake of free meso-chlorine $e_6$ monoethylene diamine disodium salt ($ce_6$) with that of nondegredable Polymer-Gly-$ce_6$ (11.2 wt % $ce_6$) (Copolymer IIIa) and with degradable Polymer-Gly-Phe-Leu-Gly-$ce_6$ (11.2 wt % $ce_6$) (Copolymer II). Five mg/kg of each respective drug were injected into the tail vein of A/J mice bearing C1300 neuroblastoma palpable tumors. The drug was first dissolved in phosphate buffered saline (PBS) at pH 7.4. The polymeric drug was more soluble in PBS than the free drug. To get the free drug into solution, either the pH had to be raised, or the solution was heated in the dark and cooled to room temperature before injection and injected immediately.

Polymer-Gly-$ce_6$ (Copolymer IIIa)/Free $ce_6$ Localization/Retention Results

As stated, when tumors were palpable, mice were injected with 5 mg/kg free $ce_6$ or Polymer-Gly-$ce_6$. Animals were sacrificed and tissue samples (tumor, skin, spleen, leg muscle, kidney, abdominal muscle, and liver) were removed at various time intervals after injection. Samples were frozen and lyophilized for two days. The dried samples were weighed. One ml of water/25 mg dried sample was added. The tissue was then mechanically homogenized and 100 µl of the homogenate were transferred to a hydrolysis tube. Fifty percent methylbenzethonium hydroxide in methanol (1 ml) was added to each tube and the tubes were evacuated. The samples were hydrolyzed in a heating block for 1 hour at 55° C. After cooling, 2 ml of 50% THF in water was added. After mixing, fluorescence was read (EX 397, EM 654) and compared to a standard curve for the calculation of $ce_6$ concentration (ng $ce_6$) in the samples. The free drug reached a maximum concentration in the tumor tissue in 1 hour compared with the polymer which was present in high concentration even after 48 hours. The results are shown in Tables 7 through 13 which follow:

TABLE 7

| Time | Tissue: Tumor | |
|---|---|---|
| | ng $ce_6$/mg tissue | |
| Hours | P—Gly-$ce_6$ | free $ce_6$ |
| 1 | 30 ± 5 | 17 ± 5 |
| 2 | 29 ± 8 | 20 ± 6 |
| 4 | 32 ± 2 | 4 ± 2 |
| 8 | 37 ± 4 | 7 ± 2 |
| 24 | 35 ± 4 | 4 ± 2 |
| 48 | 39 ± 3 | 2 |

TABLE 8

| Time | Tissue: Abdominal Muscle | |
|---|---|---|
| | ng $ce_6$/mg tissue | |
| Hours | P—Gly-$ce_6$ | free $ce_6$ |
| 1 | 5 ± 2 | 3.5 ± 1 |
| 2 | 4 ± 0.5 | 3 ± 1 |
| 4 | 5 ± 1 | 3 ± 1 |
| 8 | 7 ± 2 | 0.5 |
| 24 | 14 ± 2 | 1 |
| 48 | 8 | 1 |

TABLE 9

| Time | Tissue: Kidney | |
|---|---|---|
| | ng $ce_6$/mg tissue | |
| Hours | P—Gly-$ce_6$ | free $ce_6$ |
| 1 | 31 ± 2 | 12.5 ± 2.5 |
| 2 | 30 ± 2 | 13 ± 4 |
| 4 | 22 ± 3 | 4 |
| 8 | 15 ± 2 | 3 |
| 24 | 13 ± 1 | 3 ± 1 |
| 48 | 14 ± 3 | 2 ± 1 |

TABLE 10

| Time | Tissue: Spleen | |
|---|---|---|
| | ng $ce_6$/mg tissue | |
| Hours | P—Gly-$ce_6$ | free $ce_6$ |
| 1 | 16 ± 3 | 6 |
| 2 | 14 ± 1 | 7 ± 3 |
| 4 | 14 | 2 |
| 8 | 18 ± 3 | 2 |
| 24 | 15 ± 2 | 2 ± 1 |
| 48 | 18 ± 2 | 1 |

TABLE 11

| Time | Tissue: Liver | |
|---|---|---|
| | ng $ce_6$/mg tissue | |
| Hours | P—Gly-$ce_6$ | free $ce_6$ |
| 1 | 38 ± 4 | 73 ± 1 |
| 2 | 41 ± 2 | 62 ± 1 |
| 4 | 44 ± 2 | 6 ± 1 |
| 8 | 43 ± 5 | 7 ± 1 |
| 24 | 65 ± 6 | 8 ± 1 |
| 48 | 53 ± 5 | 7 |

TABLE 12

| Time | Tissue: Leg Muscle | |
|---|---|---|
| | ng $ce_6$/mg tissue | |
| Hours | P—Gly-$ce_6$ | free $ce_6$ |
| 1 | 3.0 ± 0.1 | 0.9 ± 0.3 |
| 2 | 2.7 ± 0.6 | 1.3 ± 0.1 |
| 4 | 2.2 ± 0.8 | 0 |
| 8 | 1.5 ± 0.2 | 0 |
| 24 | 2.6 ± 0.8 | 0 |
| 48 | 3.5 ± 0.9 | 0 |

TABLE 13

| Time | Tissue: Skin | |
|---|---|---|
| | ng $ce_6$/mg tissue | |
| Hours | P—Gly-$ce_6$ | free $ce_6$ |
| 1 | 0.7 | 0.9 |
| 2 | 1.2 | 1.9 ± 1.6 |
| 4 | 0.8 ± 0.4 | 0.1 |
| 8 | 0.9 ± 0.2 | 0 |
| 24 | 2.7 ± 0.7 | 0 |
| 48 | 4.7 ± 0.5 | 0 |

Another experiment was undertaken with the polymer in which tissue samples were taken after five days. The concentration of $ce_6$ in the tumor was still substantial (28 ng/mg tissue), although lower than for the shorter time periods.

Polymer-Gly-Phe-Leu-Gly-$ce_6$ (Copolymer II)/Free $ce_6$ Localization/Retention Results The same localization/retention procedure as was done for Polymer-Gly-$ce_6$ (Copolymer IIIa) was used for Polymer-Gly-Phe-Leu-Gly-$ce_6$ (11.2 wt % $ce_6$) (Copolymer II). In contrast with the results of the noncleavable study, the cleavable polymer shows a drastic reduction in $ce_6$ content in the tumor by 48 hours and complete clearance by 120 hours. This study provides indirect evidence of $ce_6$ cleavage from the polymer in tumor cells and shows the body's ability to clear the free $ce_6$. The results are shown in Tables 14 through 20 which follow:

TABLE 14

| Time | Tissue: Tumor ng $ce_6$/mg tissue | |
|---|---|---|
| Hours | Copolymer II | free $ce_6$ |
| 1 | 37 ± 5 | 7 |
| 2 | 32 ± 2 | 6 |
| 4 | 42 ± 6 | 5 |
| 8 | 54 ± 3 | 3 |
| 48 | 5 | 2 |
| 120 | 0 | 0 |

TABLE 15

| Time | Tissue: Abdominal Muscle ng $ce_6$/mg tissue | |
|---|---|---|
| Hours | Copolymer II | free $ce_6$ |
| 1 | 1.0 ± 0.2 | 0.2 |
| 2 | 2.3 ± 0.1 | 0.1 |
| 4 | 7.5 ± 2.0 | 0.1 |
| 8 | 10.0 ± 2.0 | 0.2 |
| 48 | 0 | 0 |
| 120 | 0 | 0 |

TABLE 16

| Time | Tissue: Kidney ng $ce_6$/mg tissue | |
|---|---|---|
| Hours | Copolymer II | free $ce_6$ |
| 1 | 24 ± 2 | 9 ± 1 |
| 2 | 21 ± 2 | 3 ± 1 |
| 4 | 19 ± 1 | 2 |
| 8 | 14 ± 1 | 1 |
| 48 | 3 ± 2 | 1 |
| 120 | 1 or 0 | 1 |

TABLE 17

| Time | Tissue: Spleen ng $ce_6$/mg tissue | |
|---|---|---|
| Hours | Copolymer II | free $ce_6$ |
| 1 | 14 ± 1 | 24 ± 3 |
| 2 | 18 ± 1 | 24 ± 3 |
| 4 | 24 ± 3 | 24 ± 3 |
| 8 | 33 ± 3 | 34 ± 3 |
| 48 | 6 ± 1 | 21 ± 3 |
| 120 | 1 | 11 ± 1 |

TABLE 18

| Time | Tissue: Liver ng $ce_6$/mg tissue | |
|---|---|---|
| Hours | Copolymer II | free $ce_6$ |
| 1 | 42 | 90 |
| 2 | 35 ± 15 | 50 ± 6 |
| 4 | 55 ± 7 | 57 ± 5 |
| 8 | 39 ± 8 | 28 |
| 48 | 8 | 31 ± 2 |
| 120 | 3 | 33 ± 4 |

TABLE 19

| Time | Tissue: Leg Muscle ng $ce_6$/mg tissue | |
|---|---|---|
| Hours | Copolymer II | free $ce_6$ |
| 1 | 1.3 ± 0.3 | 0.2 |

TABLE 19-continued

| Time | Tissue: Leg Muscle ng $ce_6$/mg tissue | |
|---|---|---|
| Hours | Copolymer II | free $ce_6$ |
| 2 | 1.2 ± 0.4 | 0.1 |
| 4 | 1.8 ± 0.8 | 0.3 ± 0.2 |
| 8 | 1.2 ± 0.3 | 0.1 |
| 48 | 0.6 ± 0.6 | 0 |
| 120 | 0 | 0 |

TABLE 20

| Time | Tissue: Skin ng $ce_6$/mg tissue | |
|---|---|---|
| Hours | Copolymer II | free $ce_6$ |
| 1 | 0.2 ± 0.1 | 0 |
| 2 | 0.1 ± 0.2 | 0 |
| 4 | 0.3 ± 0.1 | 0 |
| 8 | 0.1 ± 0.1 | 0 |
| 24 | 0 | 0 |

In vivo localization/retention experiments with the cleavable polymer (Table 14) show a rapid clearance of $ce_6$ from the tumor tissue compared with the noncleavable polymer (Table 7). This same trend is seen for the abdominal muscle, kidney, spleen, liver, leg muscle and for skin tissue (Tables 15–20 compared with Tables 8–13). The rate of cleavage in vivo may be regulated by using different oligopeptidic spacer arms. Even slower cleavage (3–4 days) may be desirable such that the copolymer not taken up by the tumor is eliminated from the rest of the body before tumor irradiation. Also, a longer time lag between injection and irradiation provides the adria (on a spacer arm with a relatively faster release rate than that with $ce_6$) more time to take effect.

The use of a polymeric carrier for a photosensitizer decreases side effects such as light ultrasensitivity after treatment because as is shown in the above localization/retention tests that a greater quantity of polymer bound drug seems to accumulate in the tumor than the free drug even without the use of a targeting moiety. This allows a lower drug dose to be administered and still have tumor retention of the necessary concentration of sensitizer.

Example 20

Photodynamic Therapy

Several PDT experiments were performed. Different drug and light doses were studied to obtain optimal treatment regimens. Various concentrations of drug were dissolved in PBS and injected into the tail vein of the mice. After a certain time lag for uptake, light (650 nm) (argon dye laser) was applied to the tumor for various time periods. (Mice were previously anesthetized with sodium pentobarbital: stock solution 6.48 mg/ml; 0.013 ml stock solution/g body weight injected). First the effects of Polymer-Gly-$ce_6$ (Copolymer IIIa) were compared with that of the free drug. Next, the antitumor effect of Polymer-Gly-$ce_6$ (Copolymer IIIa) was compared with that of the Polymer-Gly-Phe-Leu-Gly-$ce_6$ (Copolymer II) (the free drug was no longer used because the same concentration as the polymeric drugs could not be achieved due to insolubility). The day of treatment (irradiation) was considered to be day zero.

Polymer-Gly-$ce_6$ (Copolymer IIIa) vs Free $ce_6$

A PDT experiment comparing the photodynamic effects of free $ce_6$ and Polymer-Gly-$ce_6$ (11.2 wt % $ce_6$)

(4 mg/kg) Copolymer IIIa) was performed. Irradiation (500 mW/cm$^2$; 5 minutes) was applied after a 1 or 24 hour time lag for tissue uptake. The 1 hour uptake time was toxic for both groups upon irradiation. All animals in both groups died upon light administration. The results of the 24 h uptake are shown in Table 21.

TABLE 21

| Time | Mean Tumor Vol. (mm$^3$) | |
|---|---|---|
| Days | P—Gly-ce$_6$ | Control |
| 0 | 100 | 150 |
| 1 | 150 | 250 |
| 2 | 200 ± 50 | 350 ± 50 |
| 3 | 175 ± 50 | 600 ± 100 |
| 4 | 800 ± 400 | 2300 ± 100 |

The free drug behave essentially the same as the control, while Copolymer IIIa showed tumor suppression for approximately 3 days. Because of the differences in optimal tumor uptake time between the free ce$_6$ and Polymer-Gly-ce$_6$ and insolubility of the free ce$_6$ at concentration desirable for the Polymer-Gly-ce$_6$, the free drug was no longer studied.

The effect of a 48 hours uptake of Polymer-Gly-ce$_6$ and irradiation (500 mW/cm$^2$; 5 minutes) is shown in Table 22.

TABLE 22

| Time | Mean Tumor Vol. (mm$^3$) | |
|---|---|---|
| Days | P—Gly-ce$_6$ | Control |
| 0 | 100 | 100 |
| 2 | 200 | 200 |
| 4 | 300 | 400 |
| 6 | 500 ± 150 | 700 ± 100 |
| 8 | 1400 ± 200 | 2500 ± 600 |
| 10 | 1800 ± 500 | 2800 ± 600 |

Polymer-Gly-ce$_6$ (Copolymer IIIa) vs Polymer-Gly-Phe-Leu-Gly-ce$_6$; (Copolymer II)

PDT was performed in several experiments comparing the photodynamic effects of Polymer-Gly-ce$_6$ (Copolymer IIIa) and Polymer-Gly-Phe-Leu-Gly-ce$_6$ (Copolymer II). The cleavable copolymer (Copolymer II) was more potent in all cases. At a concentration of 4 mg/kg ce$_6$ (24 hours uptake) and an irradiation power of 500 mW/cm$^2$ for 5 minutes, 60% morbidity resulted in the cleavable group (autopsy showed severe liver and other internal photodynamic damage). All mice in the noncleavable group were alive. Qualitative effects such as bleaching, edema, and black scab formation were more evident in all experiments using the cleavable copolymer compared to the noncleavable one. The best results were achieved when black scab formation was apparent. When this happened, the tumor usually disappeared for a few days.

Because of the obviously greater photodynamic effect of the cleavable copolymer (Copolymer II), it was used instead of Polymer-Gly-ce$_6$ (Copolymer IIIa) for all future PDT experiments. The next step was undertaken to optimize the drug (Copolymer II) and light dose to arrive at parameters yielding maximum effect and mouse viability. A minimal drug dose with an increased light dose proved efficacious. Doses of Polymer-Gly-Phe-Leu-Gly-ce$_6$ (11.2 wt % ce$_6$) (Copolymer II): 4, 3.25, 2.5, 2, and 1 mg/kg ce$_6$ (24 hour uptake) and light of 500 mW/cm$^2$ for 10 minutes were compared. Doses from 2.5 to 4 mg/kg ce$_6$ consistently gave varied morbidity rates between 20–100%. The 1 mg/kg group drug dose was virtually ineffective with this light dose compared with the controls.

The 2 mg/kg ce$_6$ dose of Polymer-Gly-Phe-Leu-Gly-ce$_6$ (Copolymer II) (24 hour uptake) was chosen for study. The light dose (500 mW/cm$^2$) was varied from 5–20 minutes. The 20 minute group showed 60% lethality while the 5 minute group showed little effect. However, substantial effect was achieved for irradiation times of 8 minutes 20 seconds, 10 minutes, and 13 minutes 20 seconds.

The best effect with the least chance of morbidity was shown for a drug dose of 2 mg/kg Polymer-Gly-Phe-Leu-Gly-ce$_6$ (11.2 wt % ce$_6$) (Copolymer II) and a light dose of 500 mW/cm$^2$ for 10 minutes. Results of testing Copolymer II at 2 mg/kg when injected IV into the tail veins of A/J mice bearing C1300 neuroblastoma tumors and irradiated 24 h after drug administration with 650 nm light compared with a control are shown in Table 23. Black spots or bleaching was evident for all members of the treated group. No tumor was detectable for three days following treatment after which time tumors quickly grew comparable to the controls.

TABLE 23

| Hours | Mean Tumor Vol. (mm$^3$) | |
|---|---|---|
| | Copolymer II | Control |
| 0 | 100 | 100 |
| 2 | 50 | 250 |
| 4 | 0 | 400 |
| 6 | 25 | 600 ± 100 |
| 8 | 100 ± 50 | 1150 ± 200 |
| 10 | 300 ± 100 | 2000 ± 500 |
| 12 | 500 ± 200 | 3300 ± 500 |

Example 21

Mixed Chemotherapy and PDT

In these experiments either (1) Polymer-Gly-ce$_6$ (Copolymer IIIa) and Polymer-Gly-Phe-Leu-Gly-adria (Copolymer I) or (2) Polymer-Gly-Phe-Leu-Gly-ce$_6$ (Copolymer II) and Polymer-Gly-Phe-Leu-Gly-adria (Copolymer I) were dissolved together in PBS and injected IV into the tail vein of mice with palpable tumors. A two day time lag was allowed before light administration (argon dye laser) after anesthesia for the Polymer-Gly-ce$_6$ protocol (500 mW/cm$^2$; 5 minutes) whereas only one day was allowed when using Polymer-Gly-Phe-Leu-Gly-ce$_6$ (500 mW/cm$^2$; 10 minutes) due to their differences in localization/retention behavior. The day of drug injection was considered to be day zero, the day of treatment.

Mixture of Polymer-Gly-Phe-Leu-Gly-adria (Copolymer I) and Polymer-Gly-ce$_6$ (Copolymer IIIa)

Polymer-Gly-Phe-Leu-Gly-adria (7.4 wt % adriamycin HCl; 8.2 mg/kg adriamycin.HCl) (Copolymer I) and Polymer-Gly-ce$_6$ (11.2 wt % ce$_6$; 4 mg/kg) (Copolymer III) were mixed and injected IV when tumors became palpable. On day two tumors were irradiated (500 mW/cm$^2$; 5 minutes). The extra time lag was allowed to permit adriamycin more time for effect and since it was known from the localization/retention experiments that the ce$_6$ would still be present in high concentration. A 60% cure rate was obtained and cures were followed until day 54 at which time the experiment was terminated. This experiment was repeated with an average overall cure of 40%. The mixed chemotherapy plus PDT was much more effective than either drug alone.

Mixture of Polymer-Gly-Phe-Leu-Gly-adria (Copolymer I) and Polymer-Gly-Phe-Leu-Gly-ce$_6$ (Copolymer II)

Although a 2 mg/kg dose of Polymer-Gly-Phe-Leu-Gly-ce$_6$ (Copolymer II) was found to be effective in the previous PDT experiment, it was found to be toxic when used in combination with 8.2 mg/kg Polymer-Gly-Phe-Leu-Gly-adria (Copolymer I). Therefore, the Polymer-Gly-Phe-Leu-Gly-ce$_6$ dose was decreased to 1.5 mg/kg. A combination experiment was performed using 1.5 mg/kg Polymer-Gly-Phe-Leu-Gly-ce$_6$ plus 8.2 mg/kg Polymer-Gly-Phe-Leu-Gly-adria. Two uptake times (24 and 48 hours) and irradiation (500 mW/cm$^2$/10 min) were investigated. The 48 hour uptake group showed minimal effect while the 24 hour group showed substantial effect. An eighty percent long range cure rate was achieved for this group (sacrificed at 48 days).

Results of the experiment in which the Polymer-Gly-Phe-Leu-Gly-ce$_6$ and Polymer-Gly-Phe-Leu-Gly-adria were mixed and a 48 hours and uptake was allowed before irradiation showed a significant difference in PDT effect compared with the 24 hour uptake time. The reduction in tumor destruction is indirect evidence of cleavage in the tumor. Cleavage may take place in endothelial cells lining tumor capillaries and the destruction of these capillaries may prevent the tumor from receiving nutrients and lead to its destruction. However, transcytosis most likely takes place in the endothelial cells which would indicate that the cleavage actually takes place in the tumor cells and that their destruction causes tumor death. Some polymeric material may not avoid the lysosomal route in endothelial cells and both mechanisms may contribute to tumor destruction.

In any event, the data inicate that, for both the cleavable (Polymer-Gly-Phe-Leu-Gly-ce$_6$) and noncleavable (Polymer-Gly-ce$_6$) copolymers, combination therapy in a mixture with Polymer-Gly-Phe-Leu-Gly-adria is more effective than PDT or chemotherapy alone with the same doses. By combining therapies, it is possible to overcome the side effects of both drugs.

Example 22

Combination Copolymer

The combination copolymer (Copolymer IV) was dissolved in PBS and injected IV into the tail vein of mice with palpable tumors (approximate dose 3.5 mg/kg adriamycin; 1.7 mg/kg ce$_6$). A 24 hour time lag was allowed after which light of 650 nm (argon dye laser) (500 mW/cm$^2$; 10 min) was administered. Tumor volumes were monitored with reference to the treatment day (drug injection), day zero. In this experiment, the combination copolymer showed virtually no photodynamic effect. However, this may be explained on the basis that the combination copolymer (Copolymer IV) was synthesized from a precursor containing approximately 7.8 mole % of active ester groups. This copolymer contained approximately 0.9 mole % (4.2 wt %) of ce$_6$ and 2.0 mole % (7.25 wt %) of adriamycin. Using the present procedures and copolymer it was not possible to load a single copolymer with the ratio of adriamycin to ce$_6$ (5.5:1 wt ratio) which would be desired based on the results of the polymer tests using copolymer mixtures and retain solubility of the copolymer (this corresponds with 30 wt % adriamycin in order to have at least 1 molecule of ce$_6$ per polymer chain). This ratio is not possible with any side chain content with the retention of solubility in PBS. However, efforts are currently underway to increase the solubility of the polymer which may allow for greater drug loading of the polymer and provide a means to obtain the desired ratio of adriamycin to ce$_6$ as well at that of other agents.

Even though Copolymer IV did not have the desired adriamycin:ce$_6$ ratio, it was tested for therapeutic effect in vivo to see if the adriamycin (even at such a low dose) increased the therapeutic effect of the ce$_6$ which was administered at a dose of approximately 1.7 mg/kg. Because a 2 mg/kg dose of the ce$_6$ could not be exceeded (according to control studies), the actual adriamycin dose was concomitantly 3.5 mg/kg. In addition, although this copolymer contained an average of less than one molecule of ce$_6$ per polymer chain (some chains contain one or more ce$_6$ molecules), it contained more than one molecule of adriamycin per polymer chain. (These calculations are based on a distribution inherent to the distribution of molecular weight of the polymer, therefore the values of molecules per chain are not exact). The reason for the negligible response could be a result of the low dose of adriamycin, the fact that all polymer chains did not have ce$_6$ incorporated, or perhaps the activity of the two drugs is not directly comparable to the drugs bound to different copolymers (further studies may show that one drug affects the cleavage of the other). Also, this copolymer contained more degradable side chains than the control copolymers used which could have an effect on the rate of cleavage of the drugs from the copolymer by lysosomal enzymes.

While it may be possible to load a copolymer with the desired adria:ce$_6$ weight ratio, there would be less than one molecule of the ce$_6$ per polymer chain which would defeat the purpose of having a single copolymer with both drugs incorporated into a single chain. However, in a larger animal model it should be possible to increase the percentage of ce$_6$ and narrow the ratio of the two drugs which could be incorporated into the same polymer. Another resolution to this problem would be to utilize a mixture of copolymers with one copolymer containing both an anticancer drug and a photoactivatable drug (e.g., adriamycin and ce$_6$) and the other copolymer containing only the anticancer drug e.g., adriamycin). For example, a mixture of Copolymer I and Copolymer IV, each optionally containing the same targeting moiety, and administered concurrently, could provide the desired ratio of adria and ce$_6$. Similarly, a combination Copolymer IV and any other of the copolymers containing either an anticancer drug or a photoactivatable drug can be coadministered to provide desired ratios of one bioactive agent to the other. It is therefore evident that combination copolymers containing two bioactive agents can be utilized when properly formulated to provide a desired therapeutic anticancer effect.

Example 23

Receptor-Mediated Targeting of Polymer-Gly-ce$_6$ with Secretin

Studies were carried out to compare the PDT behavior of targeted Copolymer V [Polymer(secretin)Gly-ce$_6$] and non targeted Copolymer IIIa (P-Gly-ce$_6$) against C1300 (Neuro 2A) neuroblastoma cells in vitro. Neuro 2A cells ($2 \times 10^5$ cells/well) were plated in 200 $\mu$l Dulbecco's Modified Eagle Medium (12% fetal bovine serum) (MEM) in 96 well culture plates 24 hours prior to the experiment to provide a monolayer and for the cells to regenerate their receptors. One hundred μl of MEM were drawn off and 100 μl of sample (targeted or nontargeted) were added for a final concentration of 25 μg ce$_6$/ml MEM. The cells were incubated 1.5 h (37° C.; 5% CO$_2$). The MEM was removed and cells were washed 1 time with 200 μl HBSS (Hank's buffered saline solution). The supernatant was removed and 200 μl MEM were added. Cells were irradiated for either 15, 30, or 45 minutes (650 nm; 15 mW/cm$^2$) with an incandescent lamp equipped with a red filter. After irradiation, plates were incubated for 18 hours (37° C.; 5% CO$_2$) to ensure the treatment was irreversible. Ten μl (5 mg/ml) of MTT (3-(4,5-dimethylthiazol-2-yl)-2,5-diphenyl tetrazolium bromide) (Sigma) [Mosmann, J. Immunol. Methods, 65, 55(1983) and Twentyman et al., Br. J. Cancer, 56, 279(1987)] were added. The plates were incubated 4 hours (37° C.; 5% CO$_2$). Next, 175 μl of supernatant were removed taking care to not disturb the blue formazan crystals. Two hundred μl DMSO were added to each well and the solutions were resuspended 1x. The absorbance was read on an ELISA plate reader (570 nm filter). A control plate with parallel treatments was kept in the dark.

Secretin Targeted Copolymer

The results for the first experiment comparing the PDT effects of Polymer-Gly-ce$_6$ (Copolymer IIIc) vs. Polymer(secretin)Gly-ce$_6$ (Copolymer V) (25 μg ce$_6$/ml incubation concentration for 1.5 hr.) on the Neuroblastoma cell line at three different irradiation times (15, 30, or 45 minutes) was calculated. The absorbance at 570 nm is proportional to the number of live cells because only the mitochondrial dehydrogenases of live cells can reduce MTT to a blue formazan product which absorbs at 570 nm. The results are shown in Table 24:

TABLE 24

| | Absorbance (570 nm) | | | | | |
|---|---|---|---|---|---|---|
| | Copolymer IIIc | | | Copolymer V | | |
| | Minutes of Irradiation | | | | | |
| Control | 15 | 30 | 45 | 15 | 30 | 45 |
| 1.6 | 1.7 | 1.6 | 1.7 | 1.3 | 0.4 | 0.3 |

The Polymer-Gly-ce$_6$ (Copolymer IIIc) had virtually no effect at this concentration while the targeted copolymer (Copolymer V) showed an irradiation time dependent cytotoxic effect.

A second study was performed using a RIF (radio induced fibrosarcoma) as a control (no evidence to indicate existence of a secretin receptor). Two different cell numbers for each cell line with two different incubation times (15 or 45 minutes) were investigated. For the RIF control, 5×10$^4$ cells/well and 1×10$^4$ cells/well, and for the Neuro 2A cell line the high plating density of 2×10$^5$ cells/well and the low density of 5×10$^4$ cells/well were studied. The same procedure as described above was followed, however for the cells plated at high density, the MTT incubation period was shortened to 2 hours to eliminate the possibility of the absorbance readings going offscale for the ELISA reader. Also a different ELISA reader was used for these plates which could only read the absorbance at 560 nm as opposed to 570 nm. However this had no bearing as samples were compared only to their controls.

The results of the nonspecific cell line (RIF) (without secretin receptors) which was used as a control are shown in Tables 25 and 26 which follow.

TABLE 25

| | Absorbance (570 nm) | | | |
|---|---|---|---|---|
| | RIF 5 × 10$^4$ cells/well | | | |
| | Copolymer IIIc | | Copolymer V | |
| | Minutes of Irradiation | | | |
| Control | 15 | 45 | 15 | 45 |
| 1.3 | 1.3 | 1.1 | 1.4 | 1.1 |

TABLE 26

| | Absorbance (570 nm) | | | |
|---|---|---|---|---|
| | RIF 1 × 10$^4$ cells/well | | | |
| | Copolymer IIIc | | Copolymer V | |
| | Minutes of Irradiation | | | |
| Control | 15 | 45 | 15 | 45 |
| 0.63 | 0.63 | 0.57 | 0.75 | 0.52 |

Neither the targeted (Copolymer V) nor the nontargeted polymer (Copolymer IIIc) (25 μg ce$_6$/ml incubation concentration) were cytotoxic at the 15 minute irradiation time. The 45 minute irradiation time for both copolymers showed some cytotoxicity. The targeted copolymer seemed to be a little more potent which may be a result of nonspecific interaction of the hormone with the cell surface. On the other hand, the targeted copolymer had a marked time dependent cytotoxic effect on the Neuro 2A cells which was especially pronounced for the lower cell density. The nontargeted Polymer-Gly-ce$_6$ (at the same incubation concentration) had no effect on the cells for either irradiation time. These results are shown in Tables 27 and 28.

TABLE 27

| | Absorbance (570 nm) | | | |
|---|---|---|---|---|
| | Neuro 2A2 2 × 10$^5$ cells/well | | | |
| | Copolymer IIIc | | Copolymer V | |
| | Minutes of Irradiation | | | |
| Control | 15 | 45 | 15 | 45 |
| 1.6 | 1.7 | 1.8 | 1.3 | 0.5 |

TABLE 28

| | Absorbance (570 nm) | | | |
|---|---|---|---|---|
| | Neuro 2A2 5 × 10$^4$ cells/well | | | |
| | Copolymer IIIc | | Copolymer V | |
| | Minutes of Irradiation | | | |
| Control | 15 | 45 | 15 | 45 |
| 1.7 | 1.7 | 1.8 | 1.2 | 0.2 |

The results of the cytotoxicity assays comparing the PDT effects of Copolymer V and Copolymer IIIc shows positive indication of the existence of a secretin receptor in the Neuro 2A tumor line used in these studies. Selective PDT does take place in vitro. PDT is specific for the Neuro 2A cell line as incubation of the RIF cell line shows only minimal effect at only the highest irradiation time (45 minutes) compared with a drastic reduction in live cells for the Neuro cell line. The above provides evidence that secretin, along with other targeting determinants mentioned above in U.S. Pat. No. 5,037,883, may function as a targeting moiety for the copolymer combinations of this invention.

Although this invention has been described and illustrated in the above examples, these are exemplary only and the invention is limited only in scope by the following claims and the functional equivalents thereof. The compositions of this invention are intended for use in the treatment of cancerous tissues in warm-blooded animals which is inclusive of use in humans. The active agents, whether anticancer agents or photoactivatable agents, whenever named specifically or by class are considered to be inclusive of derivatives of such agents as are known to those skilled in that art. For example, the photoactivatable agents enumerated, i.e. porphyrins, phthalocyanines, purpurins, chlorins, napthalocyanines, cationic dyes, and tetracyclines are inclusive of derivatives of these classes of compounds. Specifically, the photoactive agent illustrated, meso-chlorin $e_6$, is a chlorin derivative. Since the invention is not drawn to novel therapeutic drugs per se, but rather to a carrier system to enhance the availability of such drugs at cell specific sites where maximum effect can be achieved, many other active agents, substitutions, modifications, or derivatives may be utilized and still be within the scope of the present invention.

---

We claim:

1. A composition for the treatment of cancerous tissues in warm-blooded animals containing both an anticancer drug and a photoactivatable drug attached to copolymeric carriers comprising a member selected from the group consisting of (a) a copolymeric carrier having attached thereto both an anticancer drug and a photoactivatable drug, (b) a mixture of copolymeric carriers wherein one copolymeric carrier has attached thereto an anticancer drug and the other copolymeric carrier has attached thereto a photoactivatable drug and (c) a mixture of polymeric carriers wherein one copolymeric carrier has attached thereto both an anticancer drug and a photoactivatable drug and the other copolymeric carrier has attached thereto a member selected from the group consisting of an anticancer drug and a photoactivatable drug, with the proviso that said anticancer drug is attached to said polymeric carrier by side-chains which are stable in the blood stream of said warm-blooded animal but susceptible to hydrolysis by lysosomal enzymes intracellularly and wherein said polymeric carriers optionally contain a targeting moiety.

2. A composition according to claim 1 wherein said polymeric carrier is made up of copolymerized comonomer units comprising (a) between about 5.0 to 99.7 mol % of underivatized comonomer units, (b) between about 0.2 to 20.0 mol % of derivatized comonomer units having attached thereto a member selected from the group consisting of said anticancer agent and said photoactivatable agent; and (c) between about 0 to 94.8 mol % of derivatized comonomer units containing said targeting moiety.

3. A composition according to claim 2 wherein said polymeric carrier contains between about 0.1 to 94.8 mol % of derivatized comonomer units containing said targeting moiety.

4. A composition according to claim 2 wherein said polymeric carrier is a copolymer containing underivatized and derivatized comonomer units selected from the group consisting of N-(2-hydroxypropyl)methacrylamide (HPMA), N-methylacrylamide, N,N-dialkylacrylamides, acrylic acid, methacrylic acid, polyamino acids, polysaccharides, copolymers containing polyethyleneoxide sequences and polyvinyl pyrrolidone-maleic anhydride copolymers.

5. A composition according to claim 4 wherein said anticancer drug is attached to said polymeric carrier by enzyme degradable side-chains selected from the group consisting of oligopeptide sequences, oligosaccharide sequences and structures similar to those in nucleic acids.

6. A composition according to claim 5 wherein said side-chain is an oligopeptide.

7. A composition according to claim 6 wherein said polymeric carrier is a copolymer prepared from the copolymerization of underivatized and derivatized comonomer units of N-(2-hydroxypropyl)methacrylamide (HPMA).

8. A composition according to claim 4 wherein said polymeric carrier is a polysaccharide.

9. A composition according to claim 8 wherein the polysaccharide is dextran.

10. A composition according to claim 4 wherein said polymeric carrier is a copolymer containing underivatized and derivatized units of polyvinyl pyrrolidone-maleic anhydride copolymers.

11. A composition according to claim 7 wherein the oligopeptide side-chain is a peptide selected from the group consisting of Gly-Gly, Gly-Phe-Gly, Gly-Phe-Phe, Gly-Leu-Gly, Gly-Val-Ala, Gly-Phe-Ala, Gly-Leu-Phe, Gly-Leu-Ala, Ala-Val-Ala, Gly-Phe-Leu-Gly (SEQ ID NO:1), Gly-Phe-Phe-Leu (SEQ ID NO:2), Gly-Leu-Leu-Gly (SEQ ID NO:3), Gly-Phe-Tyr-Ala (SEQ ID NO:4), Gly-Phe-Gly-Phe (SEQ ID NO:5), Ala-Gly-Val-Phe (SEQ ID NO:6), Gly-Phe-Phe-Gly (SEQ ID NO:7), Gly-Phe-Leu-Gly-Phe (SEQ ID NO:8), or Gly-Gly-Phe-Leu-Gly-Phe (SEQ ID NO:9).

12. A composition according to claim 11 wherein the side chain peptide is Gly-Phe-Leu-Gly (SEQ ID NO:1).

13. A composition according to claim 12 wherein said anticancer drug attached to said side-chain peptide is a member selected from the group consisting of adriamycin, daunomycin, melphalan and bleomycin and derivatives thereof.

14. A composition according to claim 13 wherein said anticancer drug is adriamycin.

15. A composition according to claim 7 wherein said photoactivatable drug is attached to said polymeric chain by a nondegradable spacer.

16. A composition according to claim 15 wherein said nondegradable spacer is a member selected from the group consisting of glycine, or ε-aminocaproic acid.

17. A composition according to claim 7 wherein said photoactivatable drug is attached to said polymeric carrier by enzyme degradable side-chains selected from the group consisting of oligopeptide sequences, oligosaccharide sequences and structures similar to those in nucleic acids.

18. A composition according to claim 17 wherein said side-chain is an oligopeptide.

19. A composition according to claim 18 wherein the oligopeptide side-chain is a peptide selected from the group consisting of Gly-Gly, Gly-Phe-Gly, Gly-Phe-Phe, Gly-Leu-Gly, Gly-Val-Ala, Gly-Phe-Ala, Gly-Leu-Phe, Gly-Leu-Ala, Ala-Val-Ala, Gly-Phe-Leu-Gly (SEQ ID NO:1), Gly-Phe-Phe-Leu (SEQ ID NO:2), Gly-Leu-Leu-Gly (SEQ ID NO:3), Gly-Phe-Tyr-Ala (SEQ ID NO:4), Gly-Phe-Gly-Phe (SEQ ID NO:5), Ala-Gly-Val-Phe (SEQ ID NO:6), Gly-Phe-Phe-Gly (SEQ ID NO:7), Gly-Phe-Leu-Gly-Phe (SEQ ID NO:8), or Gly-Gly-Phe-Leu-Gly-Phe (SEQ ID NO:9).

20. A composition according to claim 19 wherein the side chain peptide is Gly-Phe-Leu-Gly (SEQ ID NO:1).

21. A composition according to claim 19 wherein said photoactivatable drug is a member selected from the group consisting of porphyrins, phthalocyanines, purpurins, chlorins, naphthalocyanines, cationic dyes, and tetracyclines and derivatives thereof.

22. A composition according to claim 21 wherein said photoactivatable drug is a chlorin derivative.

23. A composition according to claim 22 wherein said chlorin derivative is meso-chlorin $e_6$.

24. A composition according to claim 18 wherein both said anticancer agent and said photoactivatable drug are attached to said polymer chain by an oligopeptide side-chain which is a peptide selected from the group consisting of Gly-Gly, Gly-Phe-Gly, Gly-Phe-Phe, Gly-Leu-Gly, Gly-Val-Ala, Gly-Phe-Ala, Gly-Leu-Phe, Gly-Leu-Ala, Ala-Val-Ala, Gly-Phe-Leu-Gly (SEQ ID NO:1), Gly-Phe-Phe-Leu (SEQ ID NO:2), Gly-Leu-Leu-Gly (SEQ ID NO:3), Gly-Phe-Tyr-Ala (SEQ ID NO:4), Gly-Phe-Gly-Phe (SEQ ID NO:5), Ala-Gly-Val-Phe (SEQ ID NO:6), Gly-Phe-Phe-Gly (SEQ ID NO:7), Gly-Phe-Leu-Gly-Phe (SEQ ID NO:8), or Gly-Gly-Phe-Leu-Gly-Phe (SEQ ID NO:9).

25. A composition according to claim 24 wherein said photoactivatable drug is a member selected from the group consisting of adriamycin, daunomycin, melphalan and bleomycin and derivatives thereof and said photoactivatable drug is a member selected from the group consisting of porphyrins, phthalocyanines, purpurins, chlorins, naphthalocyanines, cationic dyes, and tetracyclines and derivatives thereof.

26. A composition according to claim 25 wherein said peptide is Gly-Phe-Leu-Gly.

27. A composition according to claim 26 wherein said anticancer drug is adriamycin and said photoactivatable drug is a chlorin derivative.

28. A composition according to claim 27 wherein said chlorin derivative is meso-chlorin $e_6$.

29. A composition according to claim 4 wherein said copolymeric carrier is a polymeric carrier having both an anticancer drug and a photoactivatable drug attached to the same polymeric molecule.

30. A composition according to claim 4 wherein said polymeric carrier is a mixture of copolymeric carriers wherein one copolymeric carrier has attached thereto an anticancer drug and the other copolymeric carrier has attached thereto a photoactivatable drug.

31. A composition according to claim 4 wherein said polymeric carrier is a mixture of polymeric carriers wherein one copolymeric carrier has attached thereto both an anticancer drug and a photoactivatable drug and the other copolymeric carrier has attached thereto a member selected from the group consisting of an anticancer drug and a photoactivatable drug.

* * * * *